(12) United States Patent
Bly et al.

(10) Patent No.: US 9,469,859 B1
(45) Date of Patent: Oct. 18, 2016

(54) METHOD FOR TREATMENT OF BIOMASS

(75) Inventors: Steven T. Bly, Yankton, SD (US); David Charles Carlson, Yankton, SD (US); Jason Richard Kwiatkowski, Cleveland Heights, OH (US)

(73) Assignee: POET RESEARCH, INC., Sioux Falls, SD (US)

( * ) Notice: Subject to any disclaimer, the term of this patent is extended or adjusted under 35 U.S.C. 154(b) by 0 days.

(21) Appl. No.: 13/209,170

(22) Filed: Aug. 12, 2011

Related U.S. Application Data

(60) Provisional application No. 61/372,971, filed on Aug. 12, 2010.

(51) Int. Cl.
*C12P 7/10* (2006.01)

(52) U.S. Cl.
CPC ........................................ *C12P 7/10* (2013.01)

(58) Field of Classification Search
None
See application file for complete search history.

(56) References Cited

U.S. PATENT DOCUMENTS

| | | | |
|---|---|---|---|
| 5,407,580 | A | 4/1995 | Hester et al. |
| 5,620,877 | A | 4/1997 | Farone et al. |
| 6,406,546 | B1 | 6/2002 | Donovan et al. |
| 6,409,841 | B1 | 6/2002 | Lombard |
| 7,077,953 | B2 | 7/2006 | Ranney et al. |
| 7,138,058 | B2 * | 11/2006 | Kurth et al. ............. 210/500.38 |
| 8,815,552 | B2 | 8/2014 | Narendranath et al. |
| 2002/0153317 | A1 * | 10/2002 | Heikkila et al. ............. 210/650 |
| 2005/0203291 | A1 | 9/2005 | Svenson et al. |
| 2008/0041366 | A1 | 2/2008 | Wahnon et al. |
| 2008/0056983 | A1 | 3/2008 | Curren et al. |
| 2008/0102502 | A1 | 5/2008 | Foody et al. |
| 2009/0173339 | A1 | 7/2009 | Heikkilä et al. |
| 2010/0143839 | A1 | 6/2010 | Nosella et al. |
| 2010/0227369 | A1 | 9/2010 | Narendranath et al. |
| 2010/0233771 | A1 | 9/2010 | McDonald et al. |
| 2012/0129234 | A1 | 5/2012 | McDonald et al. |
| 2012/0178976 | A1 | 7/2012 | Hennessey et al. |
| 2013/0065289 | A1 | 3/2013 | Carlson |
| 2013/0143290 | A1 | 6/2013 | Narendranath |
| 2013/0337521 | A1 | 12/2013 | Carlson et al. |
| 2014/0024826 | A1 | 1/2014 | Narendranath et al. |
| 2014/0209092 | A1 | 7/2014 | McDonald et al. |
| 2014/0234911 | A1 | 8/2014 | Narendranath et al. |

FOREIGN PATENT DOCUMENTS

| | | |
|---|---|---|
| CN | 101787398 | 7/2010 |
| EP | 1 306 442 | 5/2003 |
| WO | 2005099854 | 10/2005 |
| WO | WO 2011/159915 | 12/2011 |
| WO | WO 2012/103281 | 8/2012 |

OTHER PUBLICATIONS

Weng et al., Separation of Acetic Acid From Xylose by Nanofiltration, Separation and Purification Technology, 67 (2009) 95-102.*
Kearney, M. "Industrial Membrane Filtration and Short-Bed Fractal Separation Systems for Separating Monomers from Heterogeneous Plant Material." Amalgamated Research Inc. Dec. 2004. 83 pages.
Yong, Xu, et al., *Membrane Separation Detoxification of Dilute-Acid Pretreatment Solution for Lignocellulosic Materials*, Abstracts of Dissertation from the 9th Chinese Forestry Youth Academic Annual Conference, Session 5, (Dec. 31, 2010): p. 210-211; including Human Translation.
U.S. Appl. No. 14/601,956, filed Jan. 2015, Kwiatkowski et al.
U.S. Appl. No. 12/827,948, filed Jun. 2010, Bootsma et al.
U.S. Appl. No. 12/716,989, filed Mar. 2010, Kwiatkowski.
U.S. Appl. No. 13/209,170, filed Aug. 2011, Bly et al.
U.S. Appl. No. 14/459,977, filed Aug. 2014, Bootsma.
U.S. Appl. No. 14/465,177, filed Aug. 2014, Narendranath et al.

* cited by examiner

*Primary Examiner* — Suzanne M Noakes
*Assistant Examiner* — Stephen Chong
(74) *Attorney, Agent, or Firm* — Kagan Binder, PLLC

(57) ABSTRACT

The subject disclosure relates to a method for producing a fermentation product from biomass that has been pre-treated in a pre-treatment system and separated into a liquid component and a first solids component. The method comprises: (a) treating the liquid component in a filtration system comprising at least one nano-filter to produce a treated liquid component, and to remove an acid from the liquid component; (b) supplying the treated liquid component, a fermenting organism, and agents to a fermentation system; (c) recovering the fermentation product from the fermentation system; and (d) supplying the acid for re-use in the pre-treatment system. In many embodiments, the biomass comprises lignocellulosic material and the liquid component comprises pentose (e.g., xylose).

25 Claims, 29 Drawing Sheets

OPERATING CONDITION

Temperature (°C)

OPERATING CONDITION

Permeate Flux Rate (LMH)

OPERATING CONDITION

Diafiltration Water to Feed Ratio

FIG. 17A
Biomass Composition

| Cob (percent) | Husks/ Leaves (percent) | Stalk (percent) | Cellulose (Glucan) (percent) | Hemicellulose | | | | Lignin (percent) | Ash (percent) |
|---|---|---|---|---|---|---|---|---|---|
| | | | | Xylan (percent) | Arabinan (percent) | Acetate (percent) | Composite (percent) | | |
| 100 | 0 | 0 | 36.0 | 33.3 | 3.6 | 3.0 | 39.9 | 14.9 | 2.2 |
| 0 | 100 | 0 | 37.2 | 25.6 | 4.9 | 2.2 | 32.7 | 13.0 | 7.7 |
| 0 | 0 | 100 | 41.7 | 22.5 | 2.4 | 2.6 | 27.5 | 18.3 | 3.7 |
| 50 | 0 | 50 | 38.8 | 27.9 | 3.0 | 2.8 | 33.7 | 16.6 | 3.0 |
| 50 | 50 | 0 | 36.6 | 29.5 | 4.2 | 2.6 | 36.3 | 14.0 | 5.0 |
| 30 | 50 | 20 | 37.7 | 27.3 | 4.0 | 2.5 | 33.8 | 14.6 | 5.3 |

FIG. 17B
Biomass Typical and Expected Composition

| | Cellulose (Glucan) (percent) (approx.) | Hemicellulose (percent) (approx.) | Lignin (percent) (approx.) | Ash (percent) (approx.) |
|---|---|---|---|---|
| Typical Range | 35-45 | 24-42 | 12-20 | 2-8 |
| Expected Range | 30-55 | 20-50 | 10-25 | 1-10 |

FIG. 18A
Pre-Treated Biomass Liquid Component Composition

| Cob (percent) | Husks/ Leaves (percent) | Stalk (percent) | Glucose (percent) | Xylose (percent) | Arabinose (percent) | Acetic Acid (ppm) |
|---|---|---|---|---|---|---|
| 100 | 0 | 0 | 0.4 | 4.8 | 0.5 | 6090 |
| 0 | 100 | 0 | 0.4 | 2.7 | 0.5 | 3400 |
| 0 | 0 | 100 | 0.4 | 4.2 | 0.4 | 6180 |
| 50 | 0 | 50 | 0.4 | 4.5 | 0.4 | 6135 |
| 30 | 50 | 20 | 0.4 | 3.6 | 0.5 | 4763 |

FIG. 18B

Pre-Treated Biomass
Liquid Component
Typical and Expected Composition

|  | Glucose (percent) (approx.) | Xylose (percent) (approx.) | Arabinose (percent) (approx.) | Acetic Acid (ppm) (approx.) |
|---|---|---|---|---|
| Typical Range | 0-1 | 2-6 | 0-1 | 3000-6400 |
| Expected Range | 0-1 | 1-8 | 0-1 | 2000-8000 |

FIG. 19A

Pre-Treated Biomass
Solids Component Composition

| Cob (percent) | Husks/ Leaves (percent) | Stalk (percent) | Cellulose (Glucan) (percent) | Hemicellulose | | | | Lignin (percent) | Ash (percent) |
|---|---|---|---|---|---|---|---|---|---|
| | | | | Xylan (percent) | Arabinan (percent) | Acetate (percent) | Composite (percent) | | |
| 100 | 0 | 0 | 60.2 | 9.5 | 0.9 | 0.3 | 10.7 | 26.7 | 1.2 |
| 0 | 100 | 0 | 54.4 | 1.3 | 0.7 | 0.7 | 10.4 | 23.8 | 9.7 |
| 0 | 0 | 100 | 51.1 | 1.4 | 1.0 | 1.0 | 15.4 | 27.3 | 3.1 |
| 50 | 0 | 50 | 55.7 | 5.5 | 0.9 | 0.6 | 13.1 | 27.0 | 2.2 |
| 50 | 50 | 0 | 57.3 | 5.4 | 0.8 | 0.5 | 10.6 | 25.2 | 5.4 |
| 30 | 50 | 20 | 55.5 | 3.8 | 0.8 | 0.6 | 11.5 | 25.4 | 5.8 |

FIG. 19B

Pre-Treated Biomass
Solids Component
Typical and Expected Composition

|  | Cellulose (Glucan) (percent) (approx.) | Hemicellulose (percent) (approx.) | Lignin (percent) (approx.) | Ash (percent) (approx.) |
|---|---|---|---|---|
| Typical Range | 48-62 | 8-17 | 22-30 | 1-10 |
| Expected Range | 45-65 | 5-20 | 20-32 | 1-10 |

FIG. 20A

| Retentate Volume (L) | Concentration Factor (estimated) | Permeate Volume (L) | Diafiltration Water Added (L) |
|---|---|---|---|
| 45 | 1 | 0 | 0 |
| 35 | 1.29 | 10 | 0 |
| 30 | 1.50 | 15 | 0 |
| 25 | 1.80 | 20 | 0 |
| 20 | 2.25 | 25 | 0 |
| 20 | 2.25 | 30 | 5 |
| 20 | 2.25 | 35 | 5 |
| 20 | 2.25 | 40 | 5 |
| 20 | 2.25 | 45 | 5 |
| 20 | 2.25 | 50 | 5 |
| 20 | 2.25 | 55 | 5 |
| 20 | 2.25 | 65 | 10 |
| 20 | 2.25 | 75 | 10 |
| 20 | 2.25 | 85 | 10 |
| 20 | 2.25 | 95 | 10 |
| 20 | 2.25 | 105 | 10 |
| 20 | 2.25 | 115 | 10 |

FIG. 20B

| | | Filmtec NF (25 °C) | Filmtec NF-270 (25 °C) | Koch SelRO MPS-34 (25 °C) | Filmtec NF-270 (32 °C) |
|---|---|---|---|---|---|
| Sulfuric Acid (percent w/v) | Before | 0.86 | 0.72 | 0.78 | 0.76 |
| | After | 0.55 | 0.53 | 0.41 | 0.58 |
| Acetic Acid (ppm) | Before | 4401 | 4291 | 4668 | 5544 |
| | After | 81 | 116 | 660 | 70 |
| Xylose (percent) | Before | 3.52 | 3.29 | 3.41 | 3.71 |
| | After | 8.5 | 7.72 | 7.31 | 9.52 |

FIG. 21A

| Cumulative Permeate Volume (L) | Retentate Volume (L) | Diafiltration Water Added (L) |
|---|---|---|
| 0 | 30 | 0 |
| 5 | 25 | 0 |
| 10 | 20 | 0 |
| 15 | 15 | 0 |
| 20 | 15 | 5 |
| 25 | 15 | 5 |
| 30 | 15 | 5 |
| 35 | 15 | 5 |
| 40 | 15 | 5 |
| 45 | 15 | 5 |
| 55 | 15 | 10 |

FIG. 21B

| | | Filmtec NF (25 °C) |
|---|---|---|
| Sulfuric Acid (percent w/v) | Before | 0.97 |
| | After | 0.89 |
| Acetic Acid (ppm) | Before | 4292 |
| | After | 214 |
| Xylose (percent) | Before | 3.58 |
| | After | 9.13 |

FIG. 22

| Fermentation time (h) | Acetic Acid (ppm) | Xylose (percent) | Ethanol (percent) | Yield (percent) |
|---|---|---|---|---|
| 0 | 5510 | 7.5 | 0.1 | 3 |
| 24 | 6540 | 5.4 | 1.6 | 30 |
| 0 | 2610 | 7.4 | 0.2 | 4 |
| 24 | 4380 | 0.8 | 4.1 | 80 |
| 0 | 1830 | 7.4 | 0.2 | 4 |
| 24 | 3730 | 0.5 | 4.1 | 81 |
| 0 | 1260 | 7.3 | 0.2 | 4 |
| 24 | 2990 | 0.2 | 4.4 | 87 |
| 0 | 640 | 8.0 | 0.2 | 3 |
| 24 | 2510 | 0.3 | 4.7 | 85 |
| 0 | 300 | 8.4 | 0.2 | 4 |
| 24 | 2160 | 0.3 | 5.1 | 87 |

FIG. 23A

| | Un-treated | | | | | |
|---|---|---|---|---|---|---|
| | 24 hr | | | 48 hr | | |
| | Ethanol (percent) | Xylose (percent) | Acetic Acid (ppm) | Ethanol (percent) | Xylose (percent) | Acetic Acid (ppm) |
| 0.1 g/L Yeast | 0.04 | 3.12 | 3682 | 0.12 | 2.87 | 3394 |
| 1.0 g/L Yeast | 1.55 | 0.24 | 3532 | 1.30 | 0.05 | 3193 |
| 10 g/L Yeast | 1.63 | 0.05 | 5045 | 1.15 | 0.05 | 6440 |

FIG. 23B

| | Concentrated | | | | | |
|---|---|---|---|---|---|---|
| | 24 hr | | | 48 hr | | |
| | Ethanol (percent) | Xylose (percent) | Acetic Acid (ppm) | Ethanol (percent) | Xylose (percent) | Acetic Acid (ppm) |
| 0.1 g/L Yeast | 0.01 | 6.71 | 5004 | 0.01 | 6.65 | 4931 |
| 1.0 g/L Yeast | 0.28 | 6.55 | 4948 | 0.25 | 6.41 | 4997 |
| 10 g/L Yeast | 1.55 | 4.65 | 5858 | 1.82 | 3.22 | 8000 |

FIG. 23C

| | Nano-Filtered | | | | | |
|---|---|---|---|---|---|---|
| | 24 hr | | | 48 hr | | |
| | Ethanol (percent) | Xylose (percent) | Acetic Acid (ppm) | Ethanol (percent) | Xylose (percent) | Acetic Acid (ppm) |
| 0.1 g/L Yeast | 0.72 | 5.71 | 486 | 2.96 | 1.18 | 842 |
| 1.0 g/L Yeast | 2.45 | 2.67 | 929 | 3.40 | 0.18 | 1156 |
| 10 g/L Yeast | 3.80 | 0.14 | 2079 | 3.26 | 0.11 | 3575 |

METHOD FOR TREATMENT OF BIOMASS

CROSS-REFERENCE TO RELATED APPLICATIONS

This application claims the benefit of U.S. Provisional Application Ser. No. 61/372,971, filed Aug. 12, 2010, and entitled "SYSTEM FOR TREATMENT OF BIOMASS", the disclosure of which is incorporated herein by reference.

FIELD

The subject disclosure relates to a method for treatment of biomass to be used in the production of ethanol. The subject disclosure also relates to a method for removal of acid from biomass following acid pre-treatment to facilitate improvement in the efficiency and yield of cellulosic ethanol production from the biomass.

BACKGROUND

Ethanol can be produced from grain-based feedstocks (e.g., corn, sorghum/milo, barley, wheat, soybeans, etc.), from sugar (e.g., from sugar cane, sugar beets, etc.), and from biomass (e.g., from cellulosic feedstocks such as switchgrass, corn cobs and stover, wood or other plant material).

Biomass comprises plant matter that can be suitable for direct use as a fuel/energy source or as a feedstock for processing into another bioproduct (e.g., a biofuel such as cellulosic ethanol) produced at a biorefinery (such as an ethanol plant). Biomass may comprise, for example, corn cobs and stover (e.g., stalks and leaves) made available during or after harvesting of the corn kernels, fiber from the corn kernel, switchgrass, farm or agricultural residue, wood chips or other wood waste, and other plant matter. In order to be used or processed, biomass will be harvested and collected from the field and transported to the location where it is to be used or processed.

In a conventional ethanol plant producing ethanol from corn, ethanol is produced from starch. Corn kernels may be processed to separate the starch-containing material (e.g., endosperm) from other matter (such as fiber and germ). The starch-containing material is slurried with water and liquefied to facilitate saccharification where the starch is converted into sugar (e.g., glucose) and fermentation where the sugar is converted by an ethanologen (e.g., yeast) into ethanol. The product of fermentation (e.g., fermentation product) is beer, which comprises a liquid component containing ethanol and water (among other things) and a solids component containing unfermented particulate matter (among other things). The liquid component and solids component of the fermentation product is sent to a distillation system. In the distillation system, the fermentation product is distilled and dehydrated into, among other things, ethanol and stillage containing wet solids (e.g., the solids component of the beer with substantially all ethanol removed) that can be dried into distillers dried grains (DDG) and sold as an animal feed product. Other co-products, for example, thin stillage and/or syrup (and oil contained in the syrup) can also be recovered from the stillage. Thin stillage can be recovered by removing a liquid component from the stillage for example by centrifugation. Syrup can be produced from thin stillage by evaporation. Water removed from the fermentation product in distillation can be treated for re-use at the plant.

In a biorefinery configured to produce ethanol from biomass such as cellulosic feedstocks, ethanol is produced from lignocellulosic material (e.g., cellulose and/or hemi-cellulose). The biomass is prepared so that sugars in the cellulosic material (such as glucose from the cellulose and xylose from the hemi-cellulose) can be accessed and fermented into a fermentation product that comprises ethanol (among other things). The fermentation product is then sent to the distillation system, where the ethanol is recovered by distillation and dehydration. Other bioproducts such as lignin and organic acids may also be recovered as co-products. Determination of how to more efficiently prepare and treat the biomass for production into ethanol will depend upon (among other things) the form and type or composition of the biomass.

SUMMARY

The subject disclosure relates to a method for producing a fermentation product from biomass that has been pre-treated in a pre-treatment system and separated into a liquid component and a first solids component. The method comprises (a) treating the liquid component in a filtration system comprising at least one nano-filter to produce a treated liquid component and to remove an acid from the liquid component; (b) supplying the treated liquid component, a fermenting organism, and agents to a fermentation system; (c) recovering the fermentation product from the fermentation system; and (d) supplying the acid for re-use in the pre-treatment system. In many embodiments, the biomass comprises lignocellulosic material and the liquid component comprises pentose (e.g., xylose).

DESCRIPTION OF THE DRAWINGS

FIG. 17A and FIG. 17B list the composition of biomass comprising lignocellulosic plant material from the corn plant according to exemplary and representative embodiments.

FIG. 18A and FIG. 18B list the composition of the liquid component of pre-treated biomass according to exemplary and representative embodiments.

FIG. 19A and FIG. 19B list the composition of the solids component of pre-treated biomass according to exemplary and representative embodiments.

FIG. 20A is an experimental design for an exemplary embodiment.

FIG. 20B lists the composition of samples from an exemplary embodiment.

FIG. 21A is an experimental design for an exemplary embodiment.

FIG. 21B lists the composition of samples from an exemplary embodiment.

FIG. 22 lists the composition of samples from an exemplary embodiment.

FIG. 23A, FIG. 23B, and FIG. 23C list the composition of samples from an exemplary embodiment.

DETAILED DESCRIPTION

One or more of the disclosed aspects provide a system for treatment of biomass. Aspects disclosed herein also provide a method for treating acid pre-treated biomass in order to remove the acid and improve the efficiency and yield of cellulosic ethanol production from the biomass. Further aspects relate to a system and/or a method that provides one or more of features to facilitate improvement in the efficiency and yield of cellulosic ethanol from biomass.

Figure 1A:
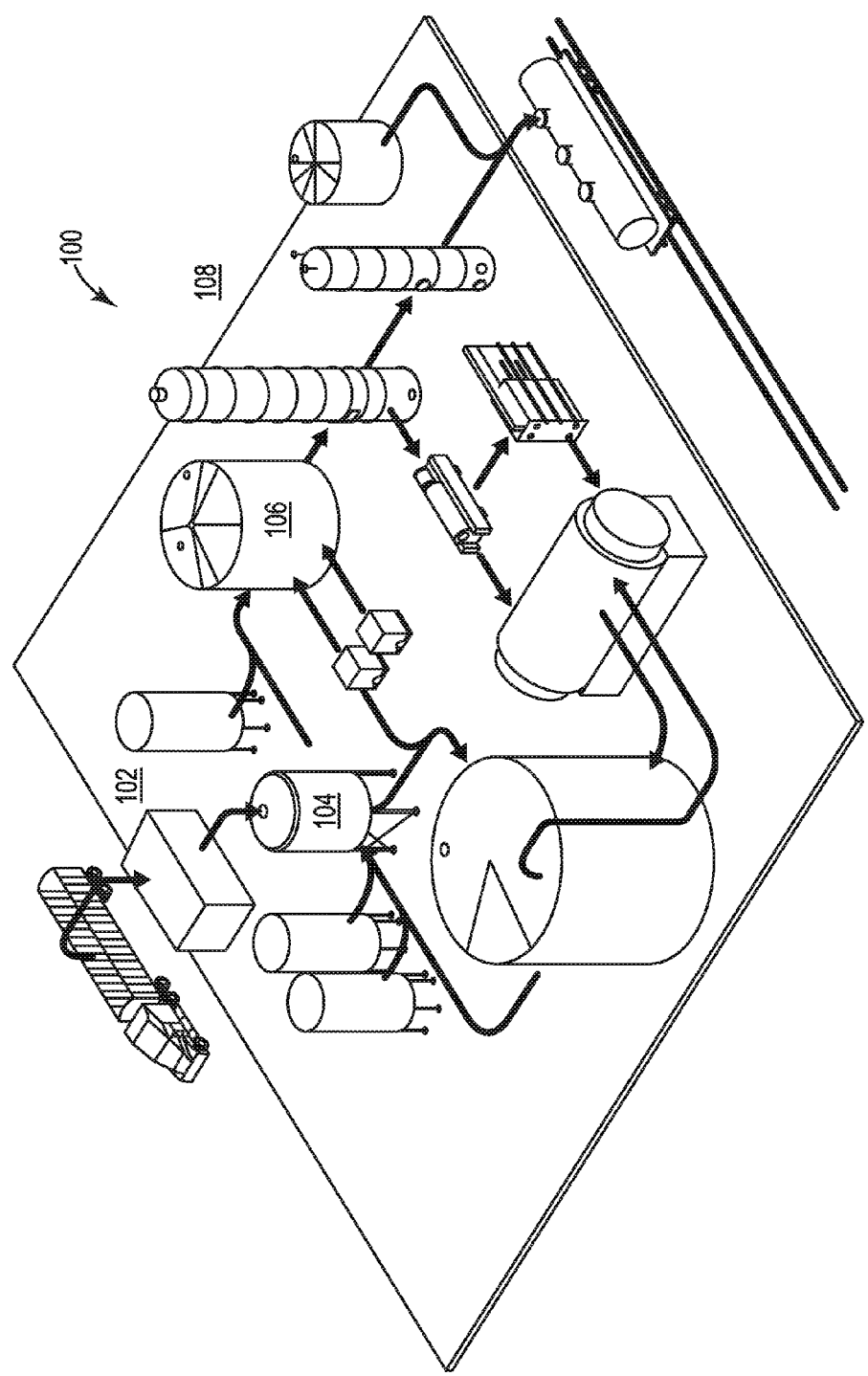
FIG. 1A is a perspective view of a biorefinery comprising a cellulosic ethanol production facility.

Referring initially to FIG. 1A, a biorefinery 100 configured to produce ethanol from biomass is shown.

According to an exemplary embodiment, the biorefinery 100 is configured to produce ethanol from biomass in the form of a lignocellulosic feedstock such as plant material from the corn plant (e.g., corn cobs and corn stover). Lignocellulosic feedstock such as lignocellulosic material from the corn plant comprises cellulose (from which C6 sugars such as glucose can be made available) and/or hemicellulose (from which C5 sugars such as xylose and arabinose can be made available).

As shown in FIG. 1A, the biorefinery 100 comprises an area where biomass is delivered and prepared to be supplied to the cellulosic ethanol production facility. The cellulosic ethanol production facility comprises an apparatus for preparation 102, pre-treatment 104 and treatment of the biomass into treated biomass suitable for fermentation into fermentation product in a fermentation system 106. The facility comprises a distillation system 108 in which the fermentation product is distilled and dehydrated into ethanol. As shown in FIG. 1A, the biorefinery may also comprise a waste treatment system 110 (shown as comprising an anaerobic digester and a generator). According to other alternative embodiments, the waste treatment system may comprise other equipment configured to treat, process, and recover components from the cellulosic ethanol production process, such as a solid/waste fuel boiler, anaerobic digester, aerobic digester or other biochemical or chemical reactors.

Figure 1B:
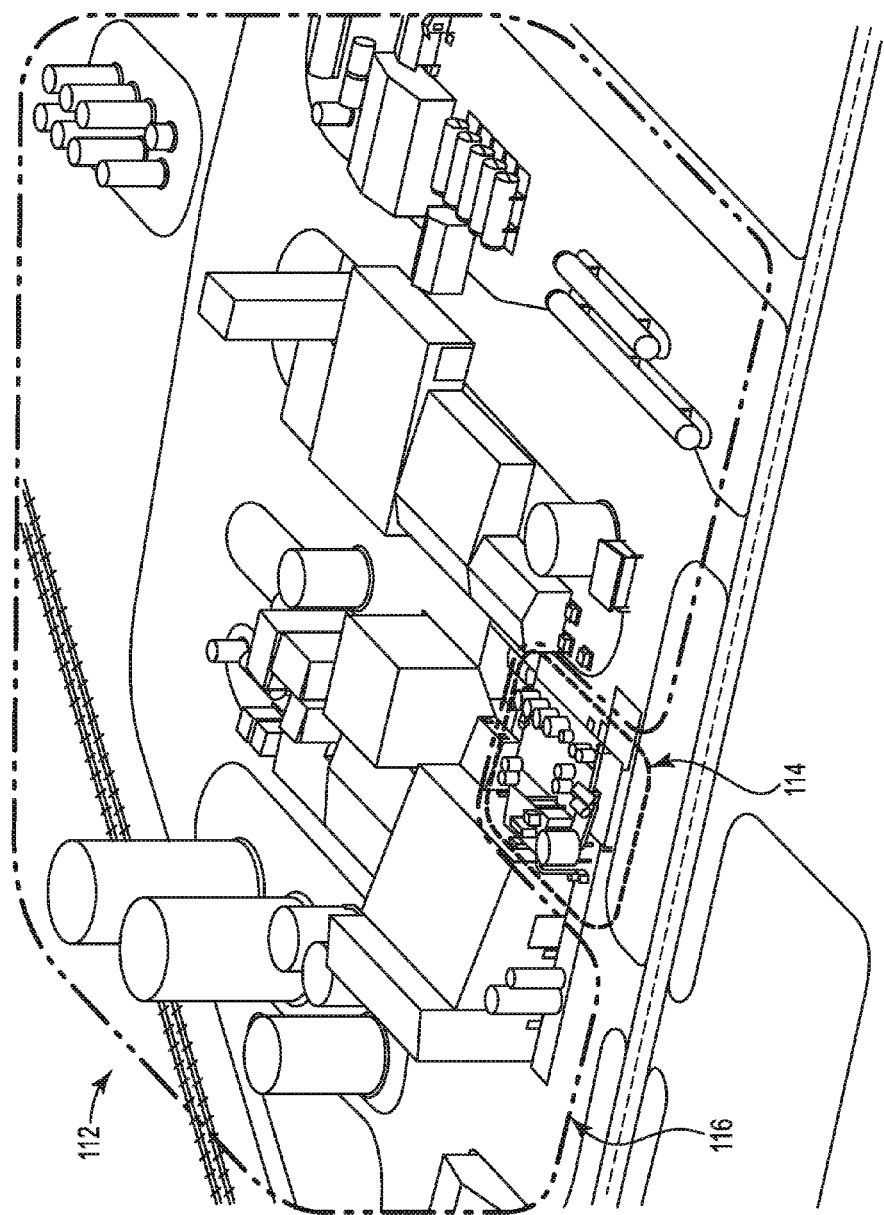
FIG. 1B is a perspective view of a biorefinery comprising a cellulosic ethanol production facility and a corn-based ethanol production facility.

As shown in FIG. 1B, according to an exemplary embodiment, a biorefinery 112 may comprise a cellulosic ethanol production facility 114 (which produces ethanol from lignocellulosic material and components of the corn plant) co-located with a corn-based ethanol production facility 116 (which produces ethanol from starch contained in the endosperm component of the corn kernel). As indicated in FIG. 1B, by co-locating the two ethanol production facilities, certain plant systems may be shared. For example, systems for dehydration, storage, denaturing and transportation of ethanol, energy/fuel-to-energy generation systems, plant management and control systems, and other systems may be shared. Corn fiber (a component of the corn kernel), which can be made available when the corn kernel is prepared for milling (e.g., by fractionation) in the corn-based ethanol production facility, may be supplied to the cellulosic ethanol production facility as a feedstock. Fuel or energy sources such as methane or lignin from the cellulosic ethanol production facility may be used to supply power to either or both co-located facilities. According to other alternative embodiments, a biorefinery (e.g., a cellulosic ethanol production facility) may be co-located with other types of plants and facilities. For example, an electric power plant, a waste treatment facility, a lumber mill, a paper plant or a facility that processes agricultural products may be co-located with the biorefinery.

Figure 2:
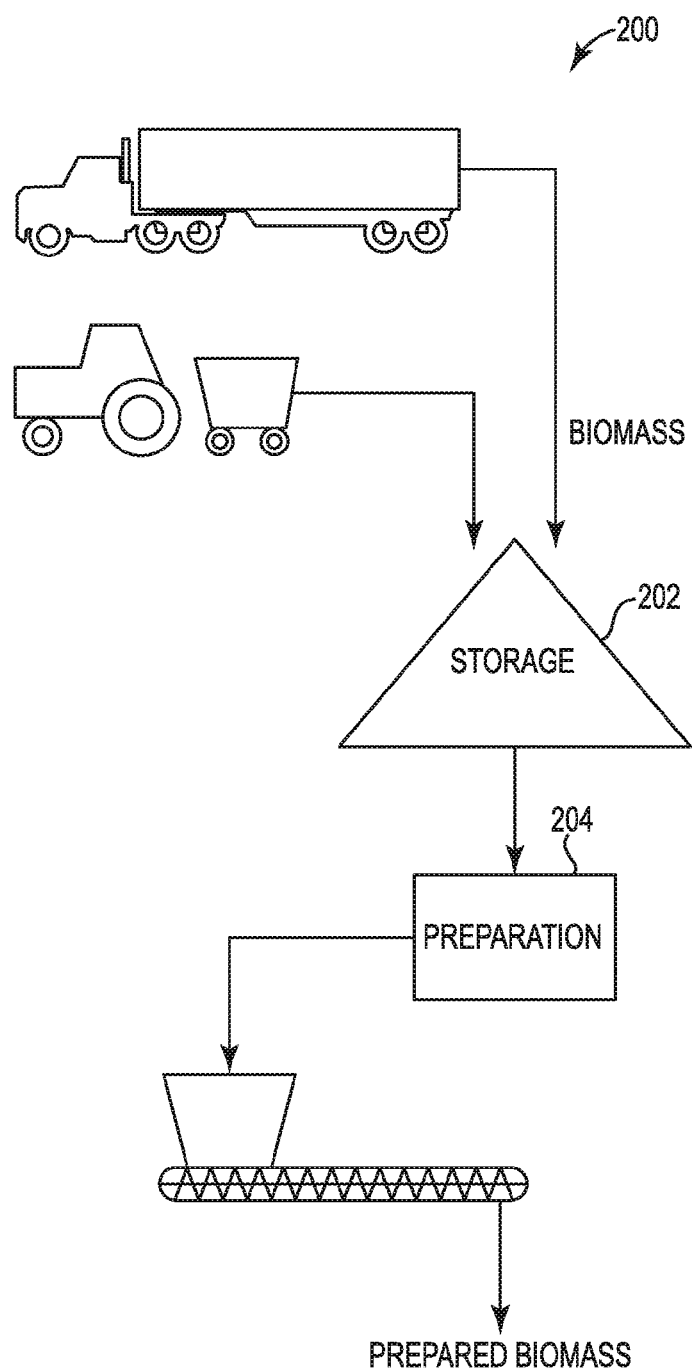
FIG. 2 is a schematic block diagram of a system for receipt and preparation of biomass for a cellulosic ethanol production facility.

Referring to FIG. 2, a system 200 for preparation of biomass delivered to the biorefinery is shown. The biomass preparation system may comprise an apparatus (or multiple apparatuses) for receipt/unloading of the biomass, cleaning (e.g., removal of foreign matter), grinding (e.g., milling, reduction or densification), and transport and conveyance for processing at the plant. According to an exemplary embodiment, biomass in the form of corn cobs and stover may be delivered to the biorefinery and stored (e.g., in bales, piles or bins, etc.), shown as storage 202, and managed for use at the facility. According to another embodiment, the biomass may comprise at least about 20 to 30 percent corn cobs (by weight) with corn stover and other matter. According to other exemplary embodiments, the preparation system 204 of the biorefinery may be configured to prepare any of a wide variety of types of biomass (e.g., plant material) for treatment and processing into ethanol and other bioproducts at the plant.

Figure 3:
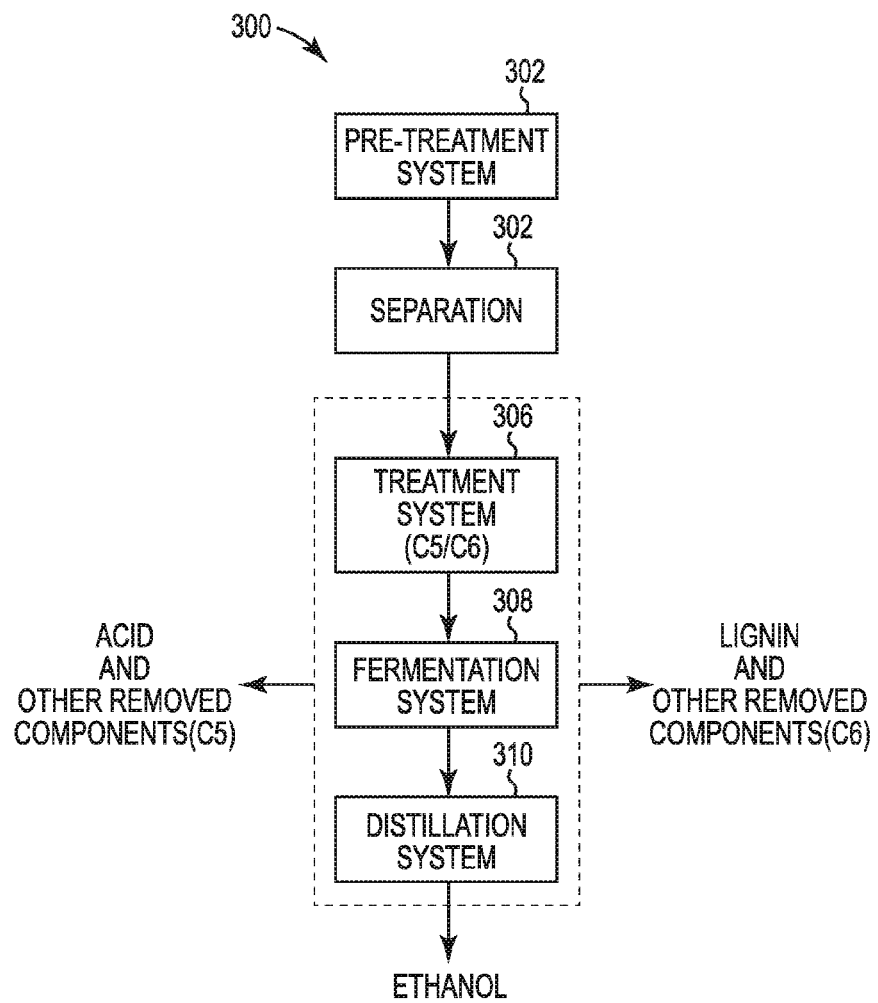
FIG. 3 is a schematic block diagram of a system for the production of ethanol from biomass.

Referring to FIG. 3, a schematic diagram of a cellulosic ethanol production facility 300 is shown. According to an embodiment, biomass comprising plant material from the corn plant is prepared and cleaned at a preparation system. After preparation, the biomass is mixed with water into a slurry and is pre-treated at a pre-treatment system 302. In the pre-treatment system 302, the biomass is broken down (e.g., by hydrolysis) to facilitate separation 304 into a liquid component (e.g., a stream comprising the C5 sugars) and a solids component (e.g., a stream comprising cellulose from which the C6 sugars can be made available). The C5-sugar-containing liquid component (C5 stream) and C6-sugar-containing solids component (C6 stream) can be treated in a treatment system 306 (as may be suitable) and fermented in a fermentation system 308. Fermentation product from the fermentation system 308 is supplied to a distillation system 310 where the ethanol is recovered.

Figures 4A, 4B, 4C:
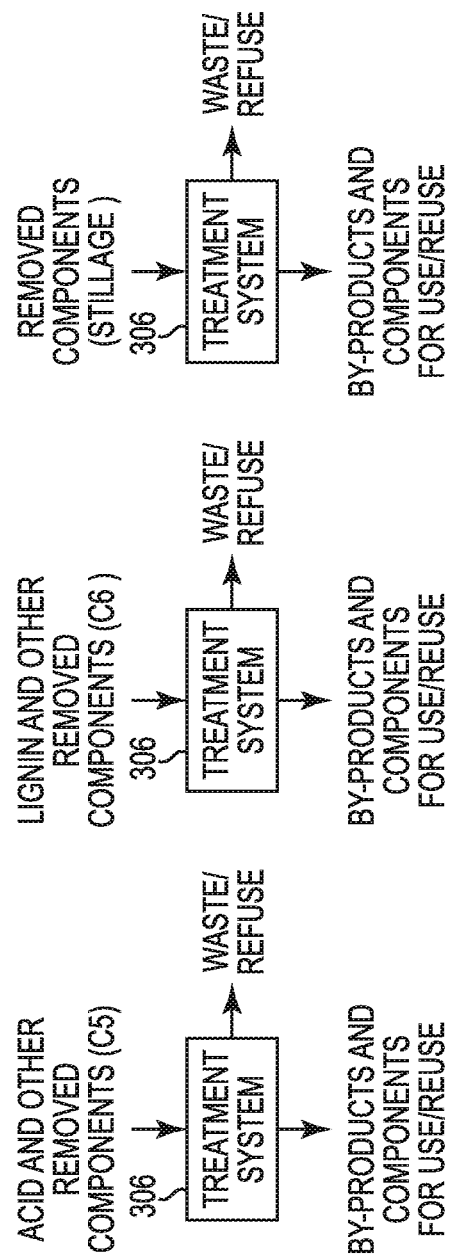
FIG. 4A, FIG. 4B, and FIG. 4C are schematic block diagrams of systems for the treatment of removed components in the production of ethanol from biomass.

As shown in FIG. 3, FIG.4A, FIG. 4B and FIG. 4C, removed components from treatment of the C5 and/or C6 stream can be treated or processed to recover by-products, such as organic acids, furfural, and lignin. The removed components during treatment and production of ethanol from the biomass from either or both the C5 stream and the C6 stream (or at distillation) can be treated or processed into bioproducts or into fuel (such as lignin for a solid fuel boiler or methane produced by treatment of residual/removed matter such as acids and lignin in an anaerobic digester) or recovered for use or reuse. As shown in FIG. 4A, FIG 4B, and FIG. 4C, components removed during treatment and production of ethanol from the biomass from either or both the C5 stream and the C6 stream (or at distillation) may be processed into bioproducts (e.g., by-products or co-products) or recovered for use or reuse. As shown in FIG. 4C, removed components from the distillation system (such as stillage or removed solids) or from the treatment of the fermentation product before distillation (e.g., removed solids and particulate matter, which may comprise residual lignin, etc.) can be treated or processed into bioproducts or fuel (e.g., methane produced in an anaerobic digester).

According to an embodiment, the biomass comprises plant material from the corn plant, such as corn cobs, husks, leaves and stalks (e.g., at least the upper half or three-quarters portion of the stalk). The composition of the plant material (e.g., cellulose, hemicellulose and lignin) will be approximately as indicated in FIG. 17A and FIG. 17B (e.g., after at least initial preparation of the biomass, including removal of any foreign matter). According to another embodiment, the plant material comprises corn cobs, husks/leaves and stalks; for example, the plant material may comprise (by weight) up to 100 percent cobs, up to 100 percent husks/leaves, approximately 50 percent cobs and approximately 50 percent husks/leaves, approximately 30 percent cobs and approximately 50 percent husks/leaves and approximately 20 percent stalks, or any of a wide variety of other combinations of cobs, husks/leaves and stalks from the corn plant. See FIG. 17A. According to an alternative embodiment, the lignocellulosic plant material may comprise fiber from the corn kernel (e.g., in some combination with other plant material). FIG. 17B provides typical and expected ranges believed to be representative of the composition of biomass comprising lignocellulosic material from the corn plant. According to exemplary embodiments, the lignocellulosic plant material of the biomass (from the corn plant) can comprise (by weight) cellulose at about 30 to 55 percent, hemicellulose at about 20 to 50 percent, and lignin at about 10 to 25 percent; according to a particular embodiment, the lignocellulosic plant material of the biomass (e.g., at least one of corn cobs, corn plant husks, corn plant leaves, and corn plant stalks or stalk portions) can comprise (by weight) cellulose at about 35 to 45 percent, hemicellulose at about 24 to 42 percent, and lignin at about 12 to 20 percent. According to another embodiment, pre-treatment of the biomass can yield a liquid component that comprises (by weight) xylose at no less than about 1.0 percent and a solids component that comprises (by weight) cellulose (from which glucose can be made available) at no less than around 45 percent.

Figure 5A:
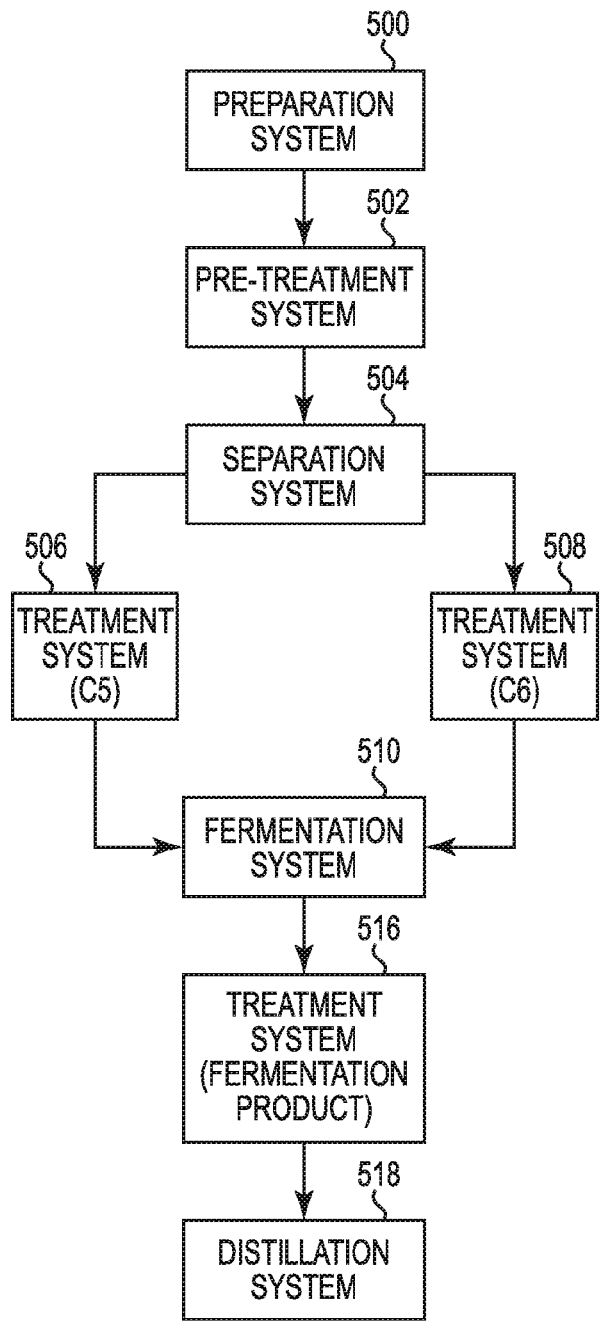
FIG. 5A and FIG. 5B are schematic diagrams of the process flow for systems for the production of ethanol from biomass.
Figure 5B:
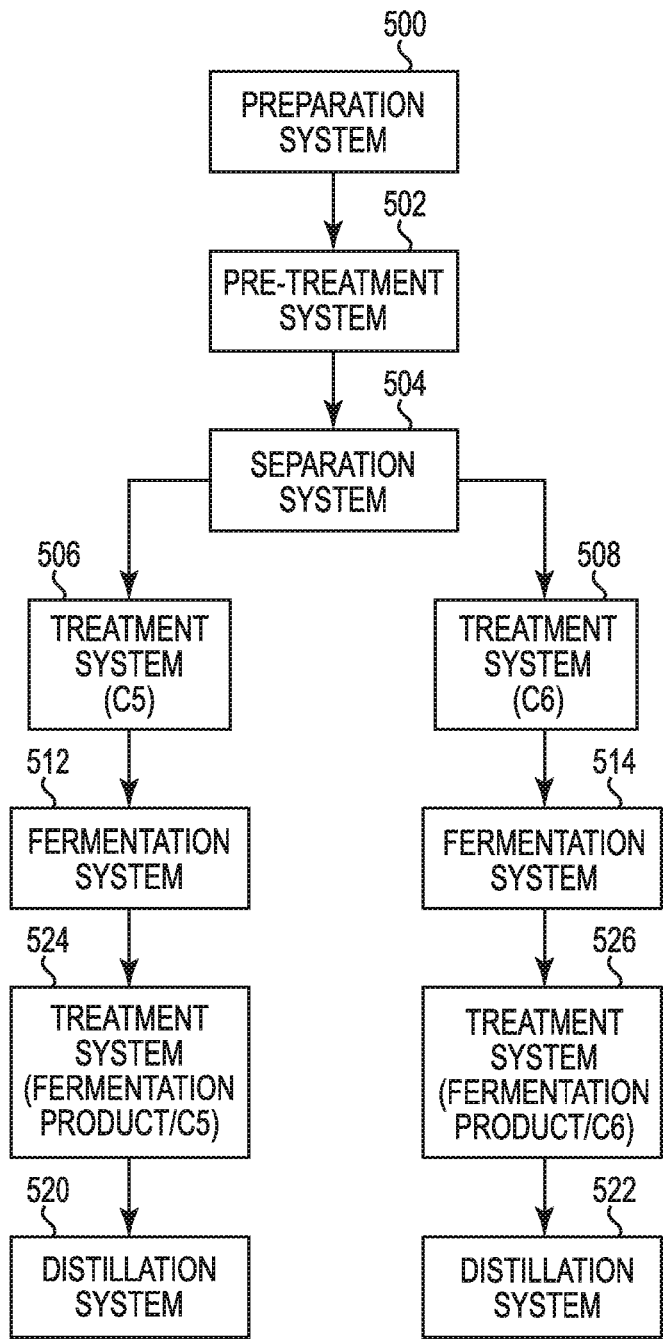

Referring to FIG. 5A and FIG. 5B, after preparation 500, pre-treatment 502, and separation 504, the C5 stream and the C6 stream are processed separately 506, 508. As shown, the C5 stream and the C6 stream may be processed separately prior to co-fermentation (C5/C6 fermentation 510 as shown in FIG. 5A) or processed separately including separate fermentation (separate C5 fermentation 512 and C6 fermentation 514 as shown in FIG. 5B).

Treatment of the C5 stream (liquid component) of the biomass may be performed in an effort to remove components that are inhibitory to efficient fermentation (e.g., furfural, hydroxymethylfurfural (HMF), sulfuric acid and acetic acid) and residual lignin (or other matter) that may not be fermentable from the C5 sugar component so that the sugars (e.g., xylose, arabinose, as well as other sugars such as glucose) are available for fermentation. The C5 sugars in the C5 stream may also be concentrated to improve the efficiency of fermentation (e.g., to improve the titer of ethanol for distillation).

Treatment of the C6 stream (solids component) of the biomass may be performed to make the C6 sugars available for fermentation. According to an embodiment, hydrolysis (such as enzyme hydrolysis) may be performed to access the C6 sugars in the cellulose. Treatment may also be performed in an effort to remove lignin and other non-fermentable components in the C6 stream (or to remove components such as residual acid or acids that may be inhibitory to efficient fermentation).

According to an exemplary embodiment shown in FIG. 5A, after preparation 500, pre-treatment 502, and separation 504, the C5 stream and the C6 stream can be treated separately (in separate treatment systems 506, 508) and subsequently combined after treatment (e.g., as a slurry) for co-fermentation in the fermentation system 510 to produce a C5/C6 fermentation product from the available sugars (e.g., xylose and glucose). The C5/C6 fermentation product can (after treatment 516, if any) be supplied to the distillation system 518 for recovery of the ethanol (e.g., through distillation and dehydration). According to an exemplary embodiment shown in FIG. 5B, the C5 stream and the C6 stream can each be separately processed through fermentation 512, 514 and distillation 520, 522 (after treatment 524, 526, if any) to produce ethanol. According to any embodiment, a suitable fermenting organism (ethanologen) can be used in the fermentation system. The selection of an ethanologen may be based on various considerations, such as the predominant types of sugars present in the slurry. Dehydration and/or denaturing of the ethanol produced from the C5 stream and the C6 stream may be performed either separately or in combination.

Figure 6A:
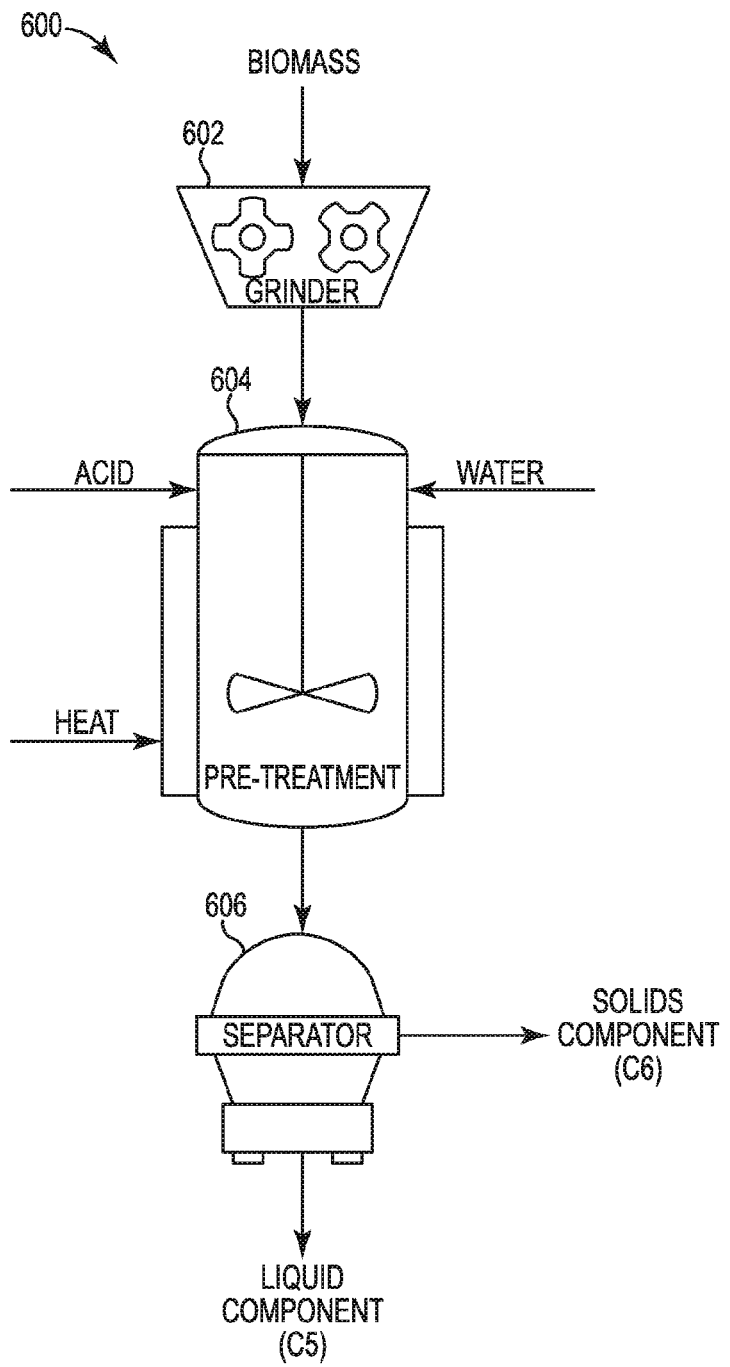
FIG. 6A is a schematic block diagram of apparatus used for preparation, pre-treatment, and separation of biomass.
Figure 6B:
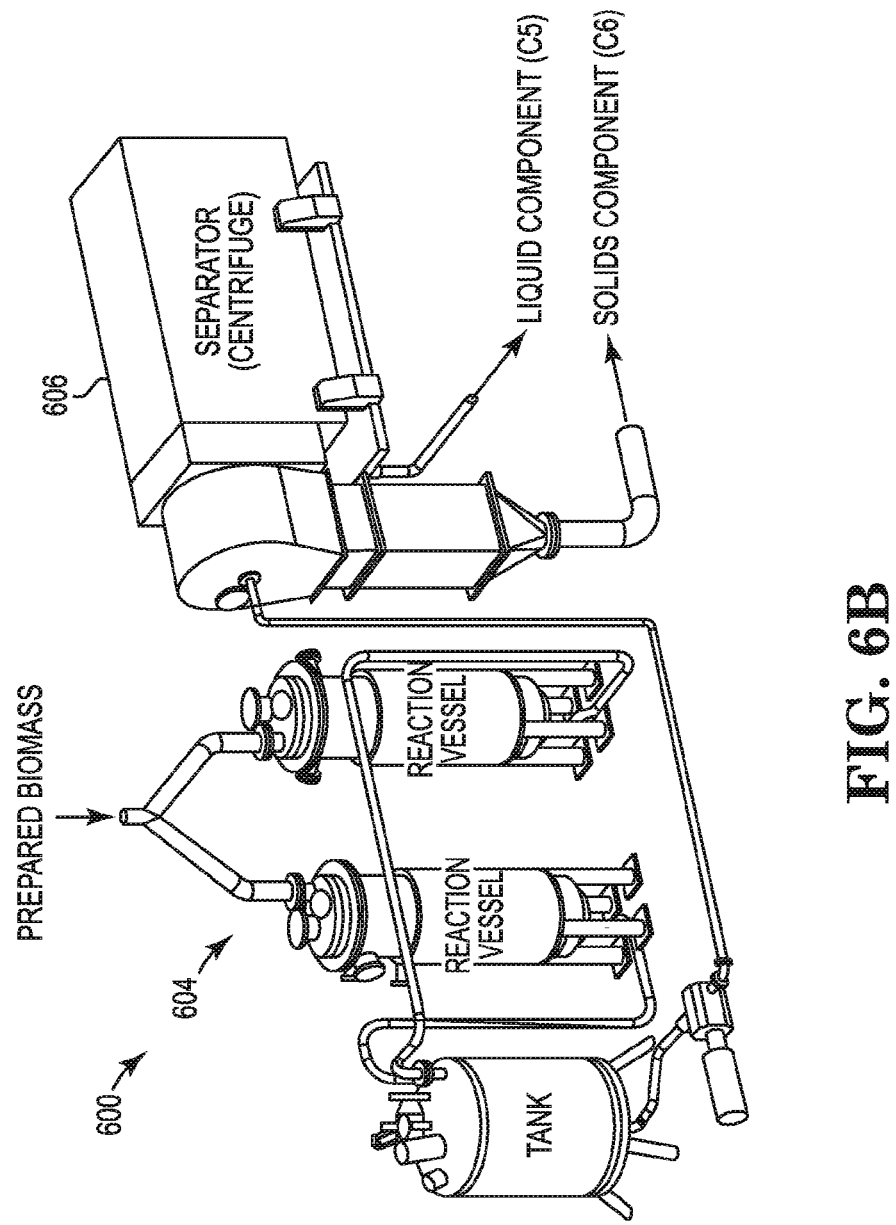
FIG. 6B is a perspective view of an apparatus used to pre-treat and separate the biomass.

FIG. 6A and FIG. 6B show the apparatus 600 used for preparation, pre-treatment, and separation of lignocellulosic biomass according to an exemplary embodiment. As shown, biomass is prepared in a grinder 602 (e.g., a grinder or other suitable apparatus or mill). Pre-treatment 604 of the prepared biomass is performed in a reaction vessel (or set of reaction vessels) supplied with prepared biomass and acid/water in a predetermined concentration (or pH) and other operating conditions. As shown in FIG. 6B, the pre-treated biomass can be separated in a centrifuge 606 into a liquid component (C5 stream comprising primarily liquids with some solids) and a solids component (C6 stream comprising liquids and solids such as lignin and cellulose from which glucose can be made available by further treatment).

According to an embodiment, in the pre-treatment system an acid can be applied to the prepared biomass to facilitate the breakdown of the biomass for separation into the liquid component (C5 stream from which fermentable C5 sugars can be recovered) and the solids component (C6 stream from which fermentable C6 sugars can be accessed). According to an embodiment, the acid can be applied to the biomass in a reaction vessel under determined operating conditions (e.g., acid concentration, pH, temperature, time, pressure, solids loading, flow rate, supply of process water or steam, etc.) and the biomass can be agitated/mixed in the reaction vessel to facilitate the breakdown of the biomass. According to some exemplary embodiments, an acid such as sulfuric acid, hydrochloric acid, nitric acid, phosphoric acid, acetic acid, etc. (or a formulation/mixture of acids) can be applied to the biomass. According to some embodiments, sulfuric acid can be applied to the biomass in pre-treatment.

The liquid component (C5 stream) comprises water, dissolved sugars (such as xylose, arabinose and glucose) to be made available for fermentation into ethanol, acids and other soluble components recovered from the hemicellulose. (FIG. 18B provides typical and expected ranges believed to be representative of the composition of biomass comprising lignocellulosic material from the corn plant.) According to an exemplary embodiment, the liquid component may comprise approximately 5 to 7 percent solids (e.g., suspended/residual solids such as partially-hydrolysed hemicellulose, cellulose and lignin). According to another embodiment, the liquid component can comprise at least about 2 to 4 percent xylose (by weight). According to other exemplary embodiments, the liquid component can comprise no less than around 1 to 2 percent xylose (by weight). FIG. 18A and FIG. 18B list the composition of the liquid component of pre-treated biomass (from prepared biomass as indicated in FIG. 17A and FIG. 17B) according to exemplary and representative embodiments.

The solids component (C6 stream) comprises water, acids, and solids such as cellulose from which sugar, such as glucose, can be made available for fermentation into ethanol and lignin. (FIG. 19B provides typical and expected ranges believed to be representative of the composition of biomass comprising lignocellulosic material from the corn plant.) According to an exemplary embodiment, the solids component may comprise approximately 10 to 40 percent solids (by weight) (after separation). According to another embodiment, the solids component can comprise approximately 20 to 30 percent solids (by weight). According to a further embodiment, the solids in the solids component can comprise no less than about 30 percent cellulose and the solids component may also comprise other dissolved sugars (e.g., glucose and xylose). FIG. 19A and FIG. 19B list the composition of the solids component of pre-treated biomass (from prepared biomass as indicated in FIG. 17A and FIG. 17B) according to exemplary and representative embodiments.

During pre-treatment, the severity of operating conditions (such as pH, temperature and time) may cause formation of components that are inhibitory to fermentation. For example, under some conditions, the dehydration of sugars (such as xylose or arabinose) may cause the formation of furfural. Acetic acid may also be formed, for example, when acetate is released during the break down of hemicellulose in pre-treatment. Sulfuric acid, which may be added to prepared biomass to facilitate pre-treatment, if not removed or neutralized, may also be inhibitory to fermentation. According to an exemplary embodiment, by adjusting pre-treatment conditions (such as pH, temperature, and time), the formation of inhibitors can be reduced or managed; according to other exemplary embodiments, components of the pre-treated biomass may be given further treatment to remove or reduce the level of inhibitors (or other undesirable matter).

Figure 7:
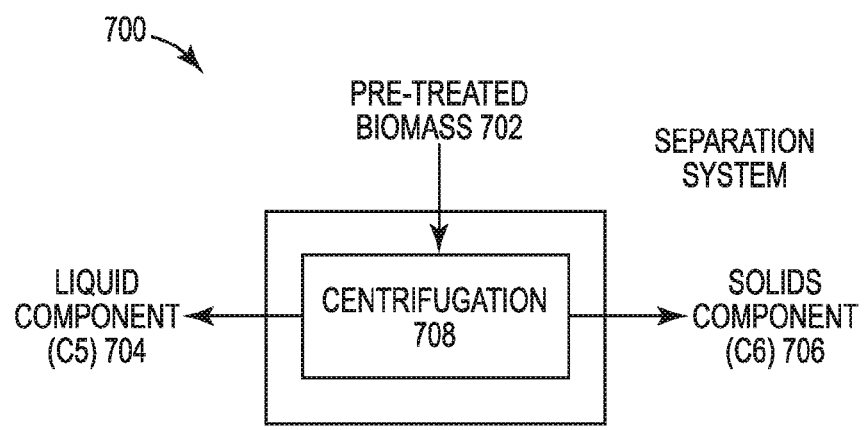
FIG. 7 is a schematic diagram of the process flow for the separation of pre-treated biomass.

FIG. 7 illustrates a schematic diagram of a process flow 700 for the separation of pre-treated biomass. As shown, pre-treated biomass 702 can be separated into a liquid component 704 and a solids component 706. In an aspect, the separation can be performed by using a centrifuge 708, for example a decanter centrifuge or a basket centrifuge.

As shown in FIG. 8A through FIG. 8D, exemplary embodiments of systems to treat (in a treatment system 800) and separate 802 the liquid component (e.g., the C5 stream) is shown. During pre-treatment, an acid (e.g., dilute sulfuric acid) has been applied to the biomass to facilitate the separation of the biomass. In separation 802, the sulfuric acid applied in pre-treatment primarily remains with the liquid component, as well as any acetic acid released from the biomass during pre-treatment. The acidity of the liquid component (which may have a pH of around 1.5) could be inhibitory to the fermentation of the sugars. The liquid component may also comprise other components that are inhibitory to fermentation, for example, chemicals such as furfural and hydroxymethylfurfural (HMF) that have formed during pre-treatment. Treatment of the liquid component (C5 stream) in the treatment system 800 is intended to remove or reduce the concentration of the inhibitory components prior to fermentation of the C5 sugars.

Figure 8A:
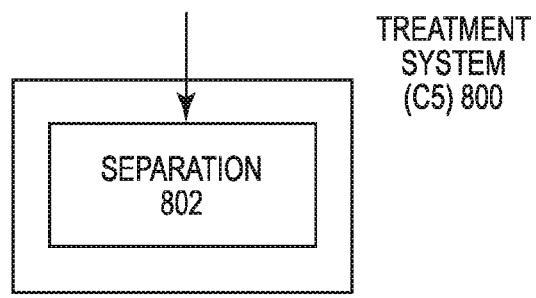
FIG. 8A, FIG. 8B, FIG. 8C, and FIG. 8D are schematic diagrams of the process flow for the treatment of pre-treated biomass liquid component (C5 stream).
Figure 8B:
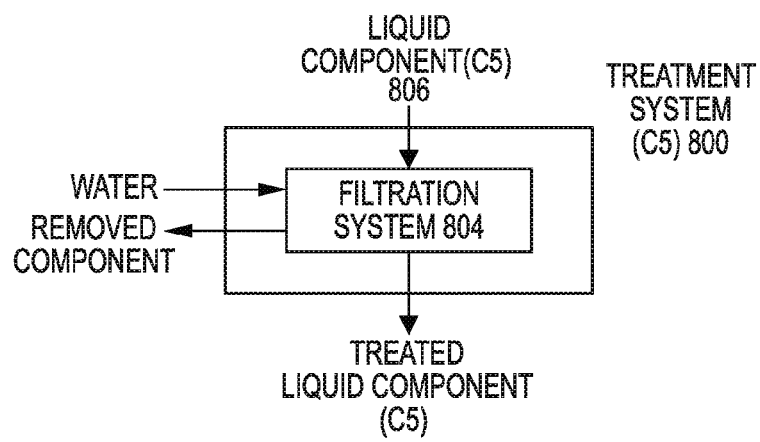
Figure 8C:
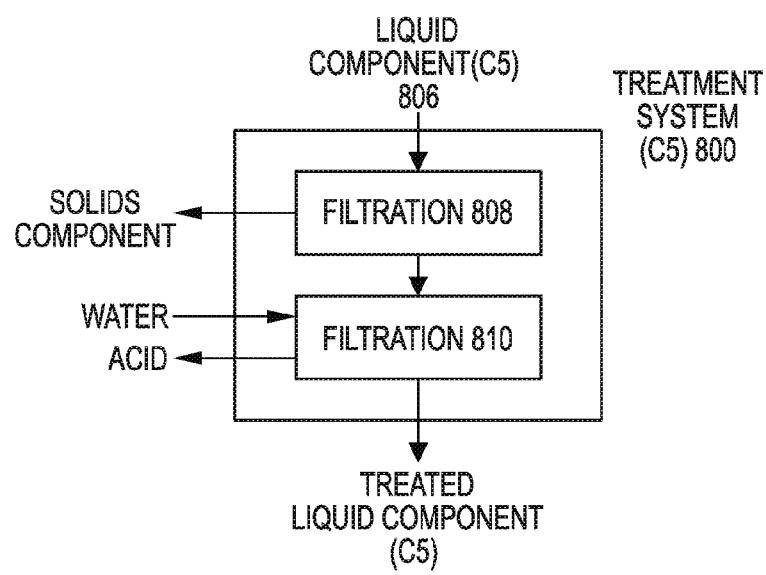

According to an embodiment shown in FIG. 8B, the treatment system 800 comprises a filtration system 804. The filtration system 804 may use one stage or multiple stages to treat the liquid component 806. Referring to FIG. 8C, the filtration system may comprise two filtration stages. The first filtration stage 808 can use a filter with a pore size of approximately 0.01 to 20 micrometers to remove solids (e.g., particulate matter) from the liquid component, or, according to some aspects, a filter with a pore size of approximately 0.1 to 10 micrometers. The second filtration stage 810 can comprise a nano-filter to retain and concentrate the volume of C5 sugars.

Figure 8D:
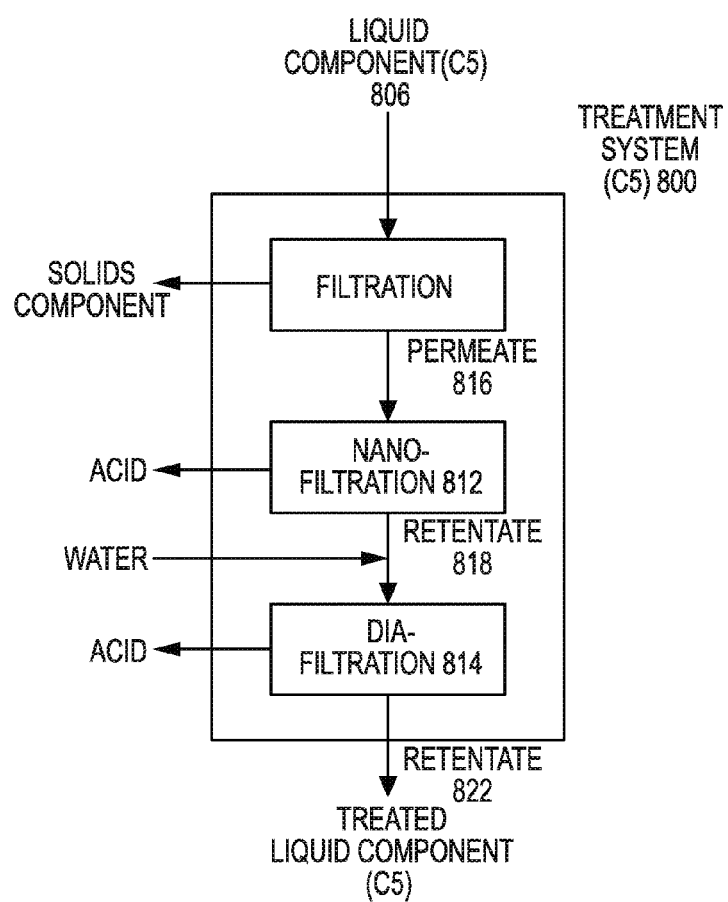
Figure 9:
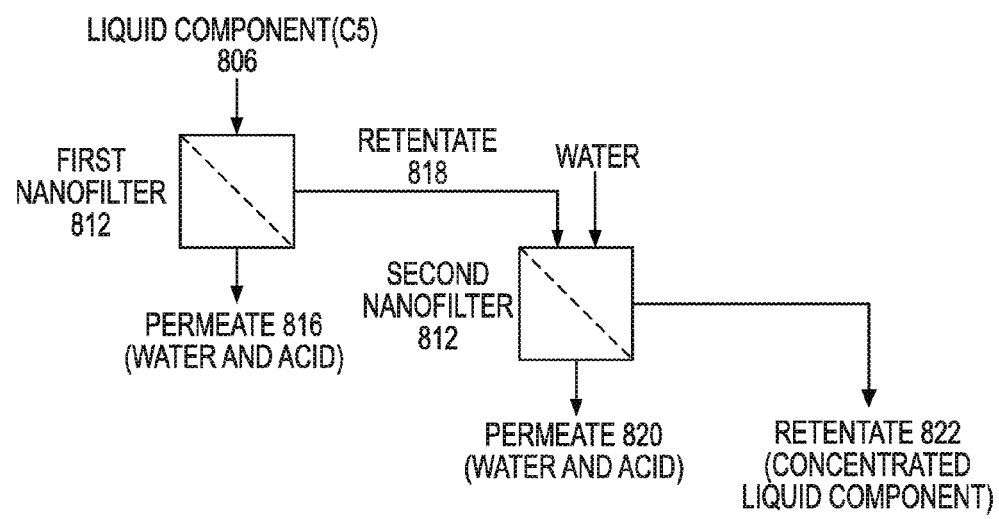
FIG. 9 is an embodiment of a treatment system for pre-treated biomass liquid component (C5 stream).

As shown in FIG. 8D, according to some embodiments, the second filtration stage (i.e., identified as 810 in FIG. 8C) can comprise a nano-filtration system configured with multiple nano-filters (e.g., two or more) or multiple filtration steps intended to remove acid and excess water from the liquid component 806, concentrating the C5 sugars (e.g., xylose) for efficient fermentation. In FIG. 8D and FIG. 9, the second filtration stage (i.e., identified as 810 in FIG. 8C) can comprise a first nano-filter 812 and a second nano-filter 814. As shown in FIG. 8D and FIG. 9, the first nano-filter 812 can have a membrane configured with pores to allow water molecules and acid ions to fit through as permeate 816 while retaining (larger molecular weight/size) sugar molecules as retentate 818. The second nano-filter 814 is configured for diafiltration in which additional water can be added to the liquid component to facilitate the flow (of water and acid) through the membrane (as permeate 820) and the retention of filtered and concentrated C5 sugars (as retentate 822).

Figure 10:
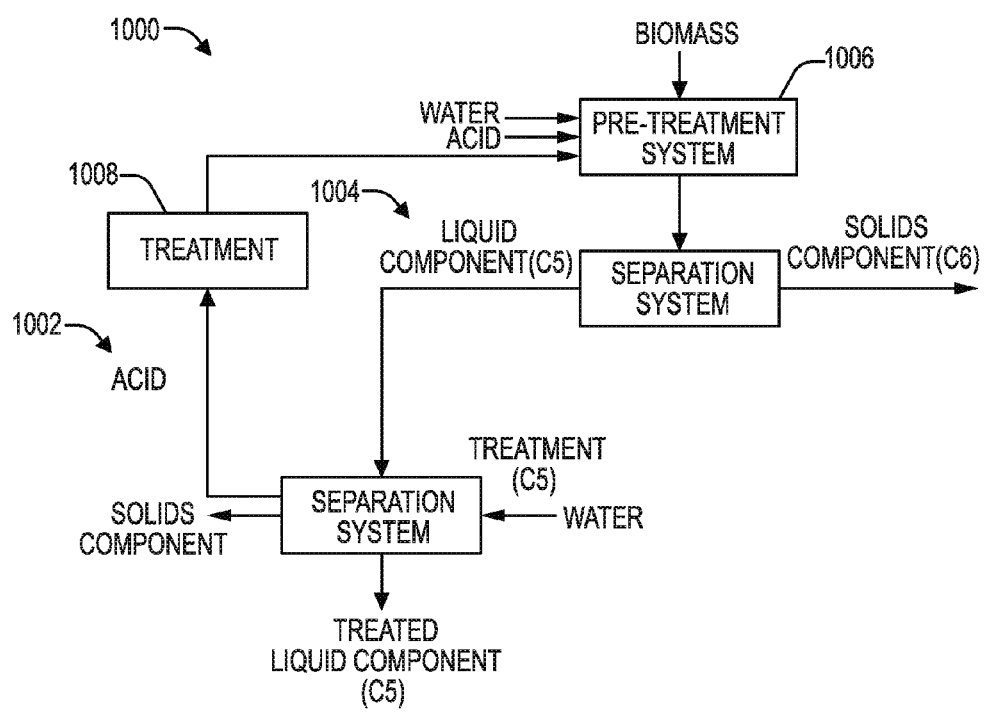
FIG. 10 is a schematic diagram of a system for treating pre-treated biomass liquid component (C5 stream).

Referring to FIG. 10, an example of a process flow 1000 where the acid is treated and re-used is shown. According to an exemplary embodiment, acid 1002 that has been removed from the liquid component 1004 can be recovered and supplied for re-use in the pre-treatment system 1006. The acid 1002 can be further treated 1008 to concentrate the acid to a desired concentration (e.g., around 2 percent). The concentration of the removed acid can be performed for example by removing water by reverse osmosis (RO).

According to some embodiments, the filtration system can comprise a filter with a pore size of less than about 10 nm. The filter may be operated under approximately 150 to 600 psi pressure to achieve a suitable feed rate. An example of a suitable filter is the Dow Filmtec NF4040, available from Dow Chemical Company in Midland, Mich. However, other filters can be utilized with the disclosed aspects.

Figure 11A:
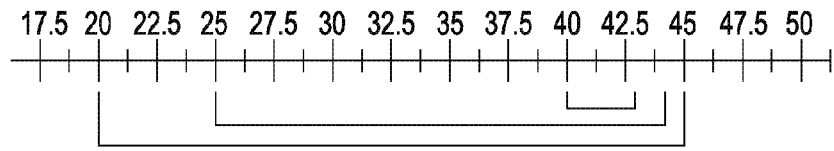
FIG. 11A, FIG. 11B, and FIG. 11C are diagrams of the operating conditions for the pre-treatment process according to an exemplary embodiment.
Figure 11B:
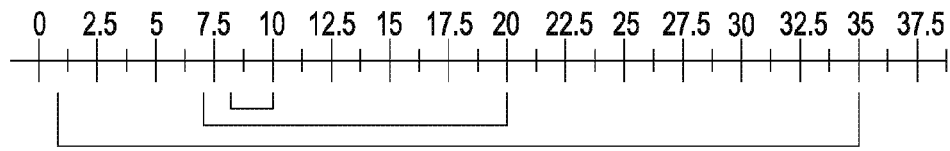
Figure 11C:
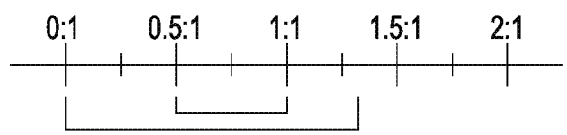

The operating conditions for subject conditions relating to the filtration system are shown in FIG. 11A, FIG. 11B, and FIG. 11C. Operating conditions for each subject condition can be indicated as "nested" ranges, comprising an acceptable operating range (the outer/wide range shown), a particular operating range (the middle range shown, if applicable), and a more particular operating range (the inner/narrow range shown, if applicable). As shown in FIG. 11A, a typical temperature range for operating the filter is from about 20° to 45° C.; a particular temperature range is around 25° to 44° C.; and a more particular range is about 40° to 43° C. As shown in FIG. 11B, a typical permeate flux rate for the first nano-filtration step is approximately 1.5 to 35 L/m$^2$/h (or LMH); a particular flux rate is about 7 to 20 LMH; and a more particular flux rate is around 8 to 10 LMH. As shown in FIG. 11C, a typical ratio of added water to liquid component feed for diafiltration is about 0 to 1.3; and a particular ratio is around 0.5 to 1.0. In some embodiments, it is desirable to conduct the nano-filtration at a low (e.g., acidic) pH. In some embodiments, the nano-filtration is conducted at a pH of about 3 or less, for example, about 1 to about 2. Conducting nano-filtration at a low pH has been observed to increase the flux rate through the filter and/or to improve the rejection rate of xylose by the filter. Conducting nano-filtration at a low pH may also be desirable in order to avoid having to add chemicals that increase the pH (e.g., basic materials such as NaOH), since these chemicals may adversely affect fermentation.

The treatment system, shown as a filtration system in FIG. 9, can be used to concentrate the sugars in the liquid component (C5 stream) by at least about 1.5 fold. According to an embodiment, the treatment system can be used to concentrate the sugars in the liquid component (C5 stream) by at least around 2 fold. According to a particular embodiment, the treatment system can be used to concentrate the sugars in the liquid component (C5 stream) by approximately 2.25 fold.

Both acetic acid (an inhibitor for fermentation) and sulfuric acid (an inhibitor for fermentation but potentially available for re-use in the pre-treatment system) can be removed from the liquid component by nano-filtration. According to an embodiment, as shown in FIG. 9, at least around 60 percent of acetic acid and at least about 40 percent of sulfuric acid can be removed from the liquid component in treatment with the nano-filtration system following acid pre-treatment (e.g., using dilute sulfuric acid) and separation of the biomass. According to an embodiment, at least around 70 percent of the acetic acid can be removed from the liquid component by use of the nano-filtration system. According to a particularly preferred embodiment, at least about 80 percent of the acetic acid and at least around 50 percent of the sulfuric acid can be removed from the liquid component by use of the nano-filtration system.

According to an embodiment of using a nano-filtration system to treat the liquid component (C5) prior to fermentation, up to about 75 percent of the available xylose in the liquid component may be converted to ethanol during fermentation. According to a preferred embodiment, about 80 percent or more of the available xylose may be converted to ethanol during fermentation, and according to a particularly preferred embodiment, about 85 percent or more of the available xylose may be converted to ethanol during fermentation.

EXAMPLES

Figure 12A:
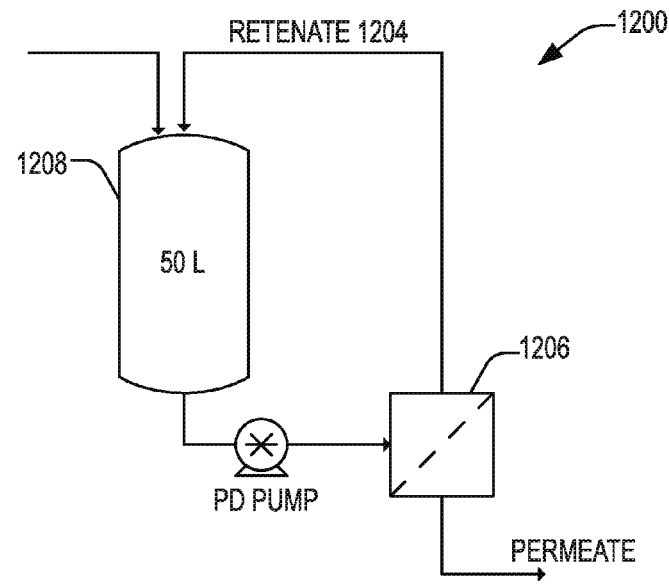
FIG. 12A is a schematic diagram of a process flow for an experimental process.
Figure 12B:
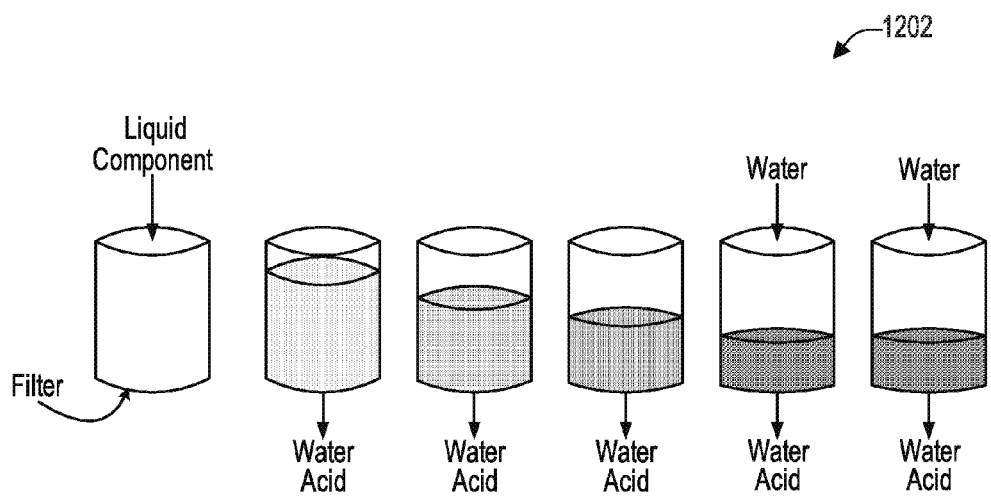
FIG. 12B is a schematic diagram of the principle of concentration and diafiltration.

A series of examples were conducted using the system as shown in FIG. 12A and FIG. 12B to test suitable filters and operating conditions. FIG. 12A illustrates a schematic diagram of a process flow for an experimental process 1200. FIG. 12B illustrates a schematic diagram 1202 of the principle of concentration and diafiltration. Prepared biomass was pre-treated and separated into a liquid component and a solids component. The liquid component was pre-filtered and used in the examples to test the effect of filtration on the composition of the liquid component (Examples 1 and 2) and on fermentation efficiency (Examples 3 and 4).

Example 1

Acid removal from the liquid component was tested according to an experimental design shown in FIG. 20A, using an experimental process 1200 shown in FIG. 12A. Three different filters were tested: Dow Filmtec NF-4040, Dow Filmtec NF-270 (both available from Dow Chemical Company, Midland Mich.), and Koch SeIRO MPS-34 (available from Koch Membrane Systems, Inc., Wilmington, Mass.). All three filters were spiral-wound membrane filters with 4-inch diameter and 40-inch length. The filters were operated at 25° C., and the Dow Filmtec NF-270 was operated at 32° C. The multi-stage nano-filtration system was modeled by the experimental process 1200 shown in FIG. 12A, where retentate 1204 from the filter 1206 can be cycled back into the storage/feed tank 1208 and filtered again (e.g., a second time) to simulate a second or consecutive stage. The principle of concentration and diafiltration is illustrated in FIG. 12B.

Figure 13A:
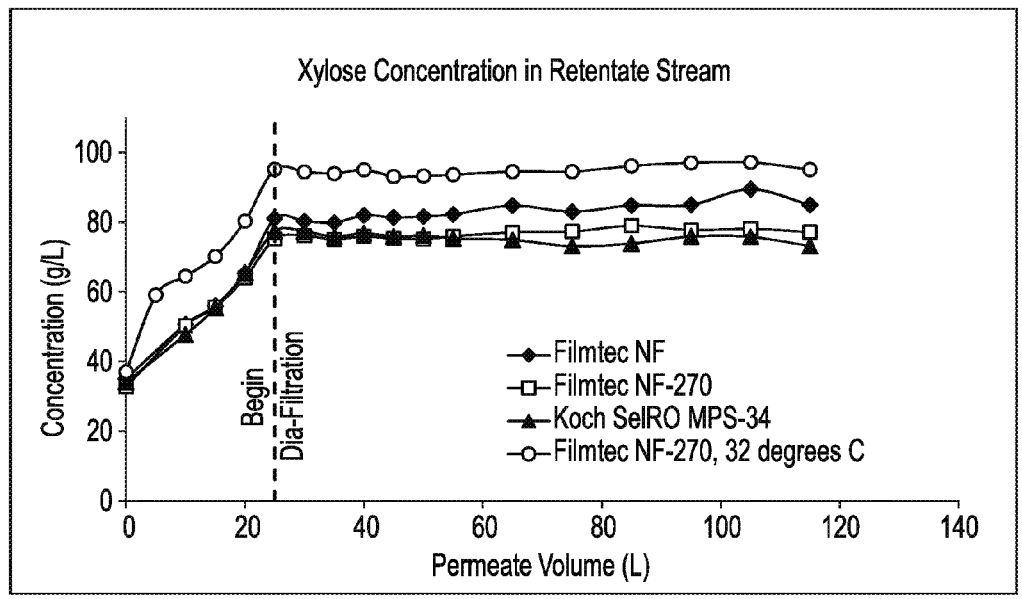
FIG. 13A, FIG. 13B, FIG. 13C, and FIG. 13D are graphs of the results of treatment of the liquid stream according to an exemplary embodiment.
Figure 13B:
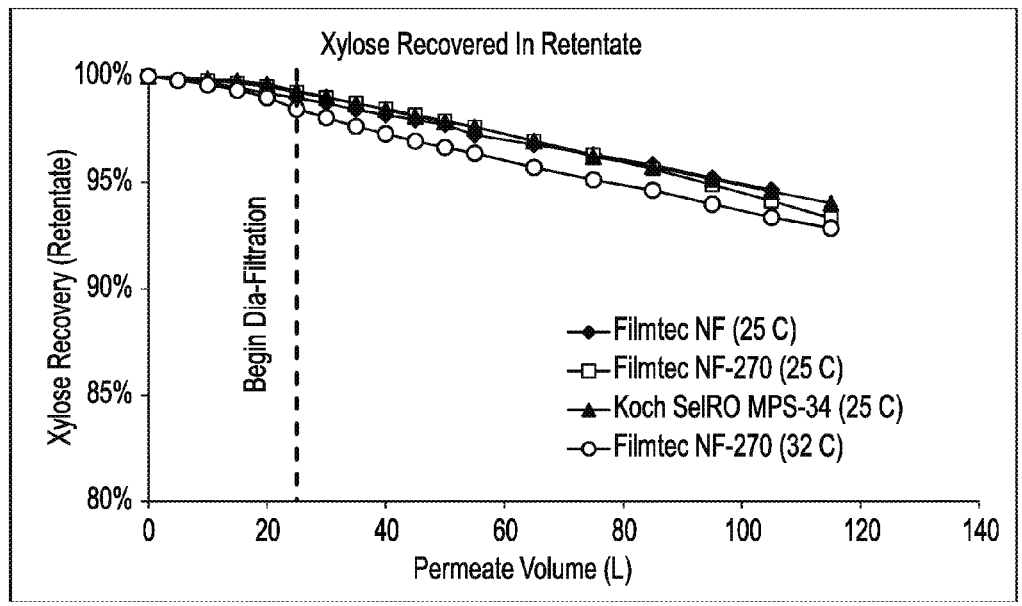
Figure 13C:
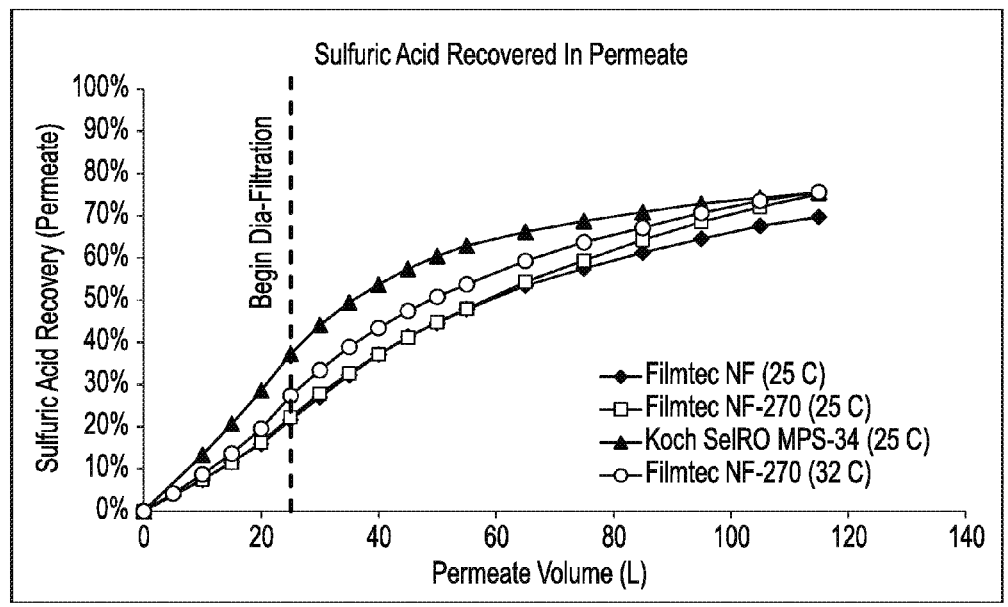
Figure 13D:
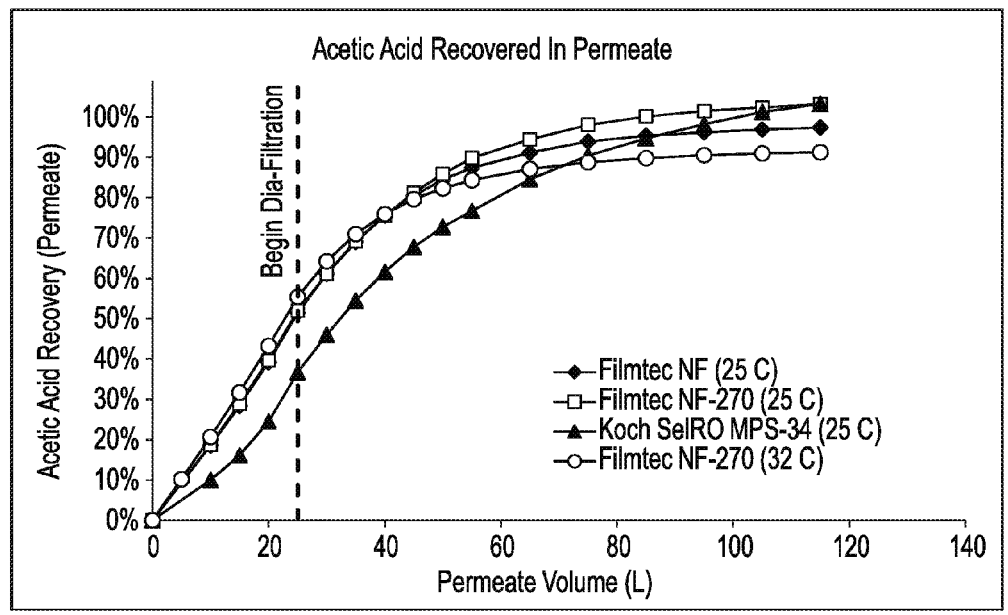

The liquid component was pre-filtered using a 10 micrometer filter. The vessel was filled with 45 L of pre-treated biomass liquid component, and approximately 1 mL of an anti-foaming agent (KFO-119, available from Kabo Chemicals, Inc., Cheyenne, Wyo.) was added to prevent foaming. The liquid component was concentrated until approximately 25 L of permeate had passed through the membrane filter, and approximately 20 L of retentate remained, yielding an estimated 2.25× concentration of sugars in the retentate. The diafiltration stage was begun by adding water to the retentate in 5 L and 10 L increments according to the experimental design (FIG. 20A). For each incremental water addition, the equivalent amount of permeate was collected causing the retentate volume to remain constant. Samples of retentate and permeate streams were collected for analysis, and the results are shown in FIG. 20B and FIG. 13A, FIG. 13B, FIG. 13C and FIG. 13D. FIG. 20B shows the concentration of sulfuric acid, acetic acid, and xylose in the liquid component retentate before and after filtration. The start of diafiltration (e.g., addition of water) is indicated in the figures when the permeate volume reached 25 L. FIG. 13A illustrates a graph of xylose concentration in the retentate, where permeate volume is represented along the horizontal axis and concentration is represented along the vertical axis. It was observed that prior to the start of diafiltration the xylose concentration increases sharply, and during diafiltration the xylose concentration remains relatively constant. FIG. 13B illustrates a graph of xylose recovery as a percentage in the retentate, where permeate volume is represented on the horizontal axis and xylose recovery (retentate) is represented along the vertical axis. FIG. 13C illustrates a graph of sulfuric acid recovery in the permeate, where permeate volume is represented on the horizontal axis and sulfuric acid recovery (permeate) is represented along the vertical axis. FIG. 13D illustrates a graph of acetic acid recovery in the permeate, where permeate volume is represented on the horizontal axis and acetic acid recovery (permeate) is represented along the vertical axis.

It was also observed that when permeate volume reached 45 L (equal to the initial volume of liquid component sample), 97 percent or more of the xylose remained in the retentate, and over 41 percent of the sulfuric acid and over 67 percent of the acetic acid was removed into the permeate. It was further observed that the Filmtec NF-270 filter was most effective in removing acetic acid with 81.3 percent of acetic acid and 41.2 percent of sulfuric acid removed and a 98.2 percent retention of xylose. The Koch SelRO filter was most effective for removing sulfuric acid with 57.4 percent of sulfuric acid and 67.8 percent of acetic acid removed and a 98.1 percent retention of xylose.

Example 2

Acid removal from the liquid component was tested according to an experimental design shown in FIG. 21A, using an experimental process shown in FIG. 12A. The experiment was conducted using a Dow Filmtec NF filter (available from Dow Chemical Company, Midland Mich.). The Dow Filmtec NF filter is a spiral-wound membrane filter with 4-inch diameter and 40-inch length. The filter was operated at ambient temperature (approximately 22° C.). The multi-stage nano-filtration system was modeled by the experimental process shown in FIG. 12A, where permeate from the filter can be cycled back into the storage/feed tank and filtered again to simulate a second or consecutive stage.

Figure 14A:
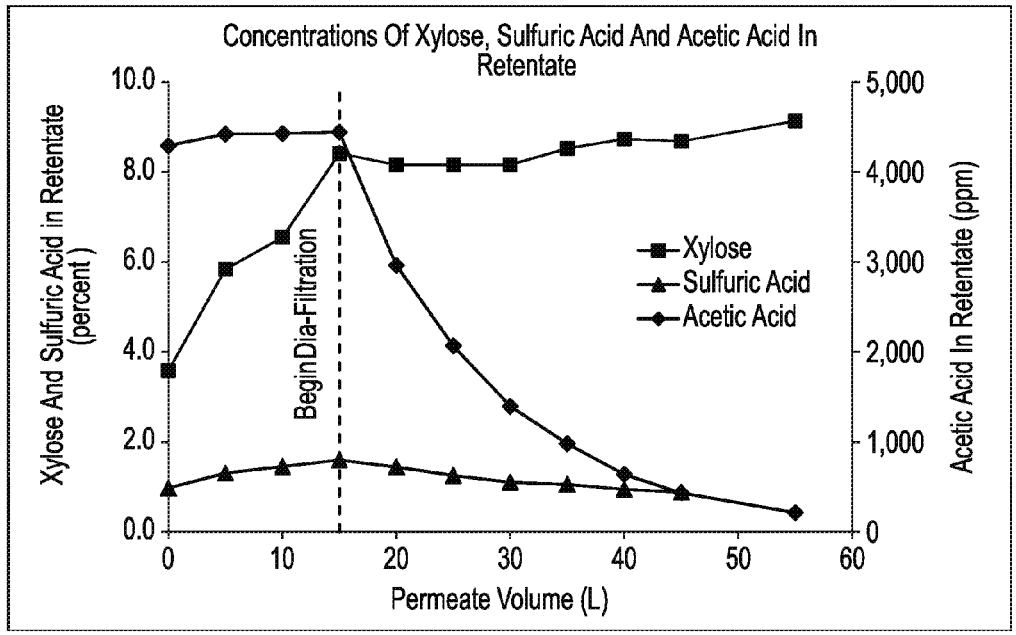
FIG. 14A and FIG. 14B are graphs of the results of treatment of the liquid stream according to an exemplary embodiment.
Figure 14B:
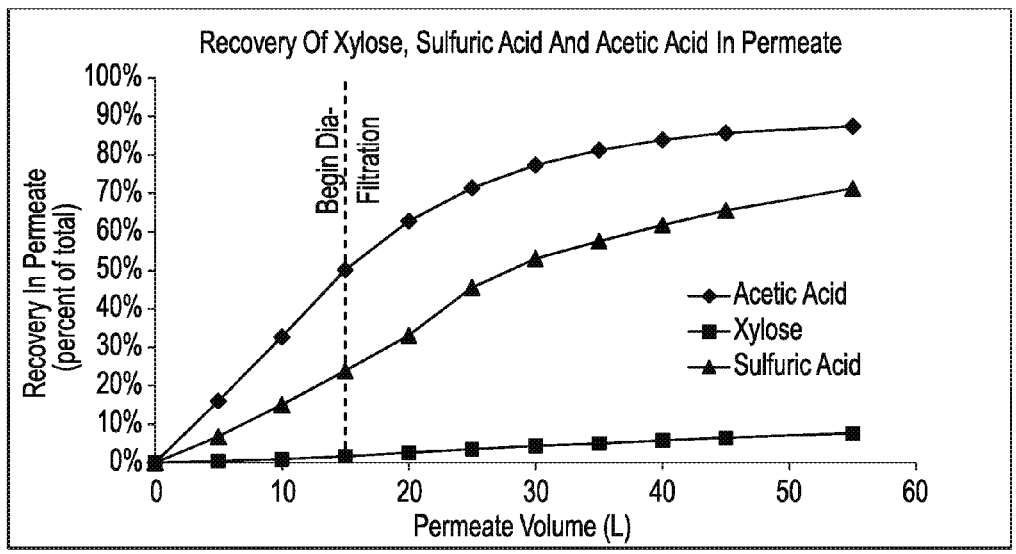

The liquid component was pre-filtered using a 1 micrometer filter. The vessel was filled with 30 L of pre-treated biomass liquid component and approximately 1 mL of an anti-foaming agent (KFO-119, available from Kabo Chemicals, Inc., Cheyenne, Wyo.) was added to prevent foaming. The liquid component was concentrated until approximately 15 L of permeate had passed through the membrane filter and approximately 15 L of retentate remained, yielding an estimated 2× concentration of sugars in the retentate. The diafiltration stage was begun by adding water to the retentate in 5 L and 10 L increments according to the experimental design (FIG. 21A). For each incremental water addition, the equivalent amount of permeate was collected causing the retentate volume to remain constant. Samples of retentate and permeate streams were collected for analysis; the results are shown in FIG. 21B and FIG. 14A and FIG. 14B. FIG. 14A shows xylose concentration, sulfuric acid concentration, and acetic acid concentration in the retentate, sulfuric acid concentration in the permeate and acetic acid concentration in the permeate, where permeate volume is represented along the horizontal axis and xylose and sulfuric acid in retentate (percent) is illustrated along the vertical axis. FIG. 14B shows xylose recovery, sulfuric acid recovery, and acetic acid recovery as a percentage in the permeate, where permeate volume is represented along the horizontal axis and recovery in the permeate (percent of total) is represented along the vertical axis. It was observed that when permeate volume reached 30 L (equal to the initial volume of liquid component sample), about 96 percent of the xylose remained in the retentate, and about 53 percent sulfuric acid and about 77 percent of acetic acid was removed to the permeate.

Example 3

Figure 15A:
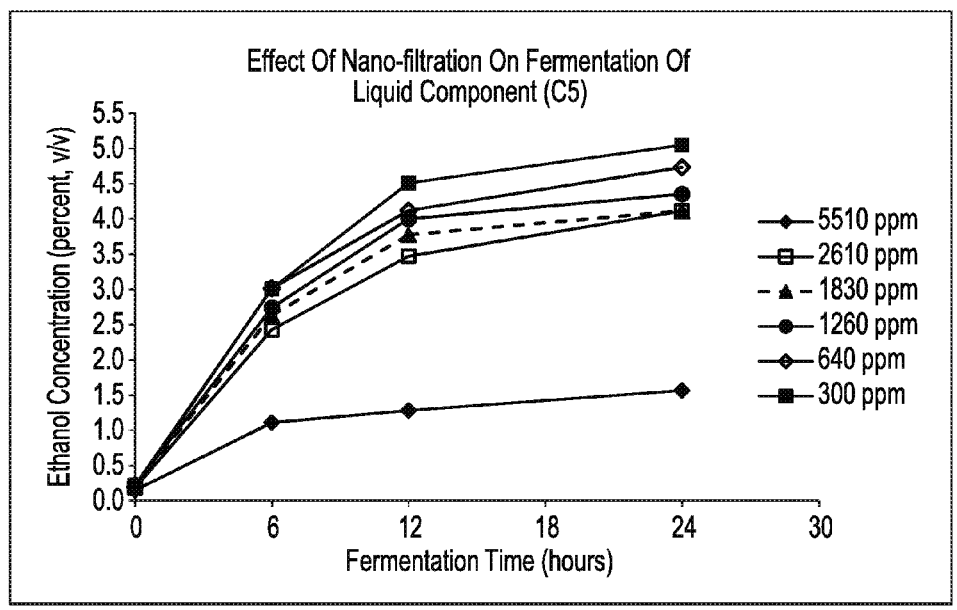
FIG. 15A and FIG. 15B are graphs of the results of treatment of the liquid component according to an exemplary embodiment.
Figure 15B:
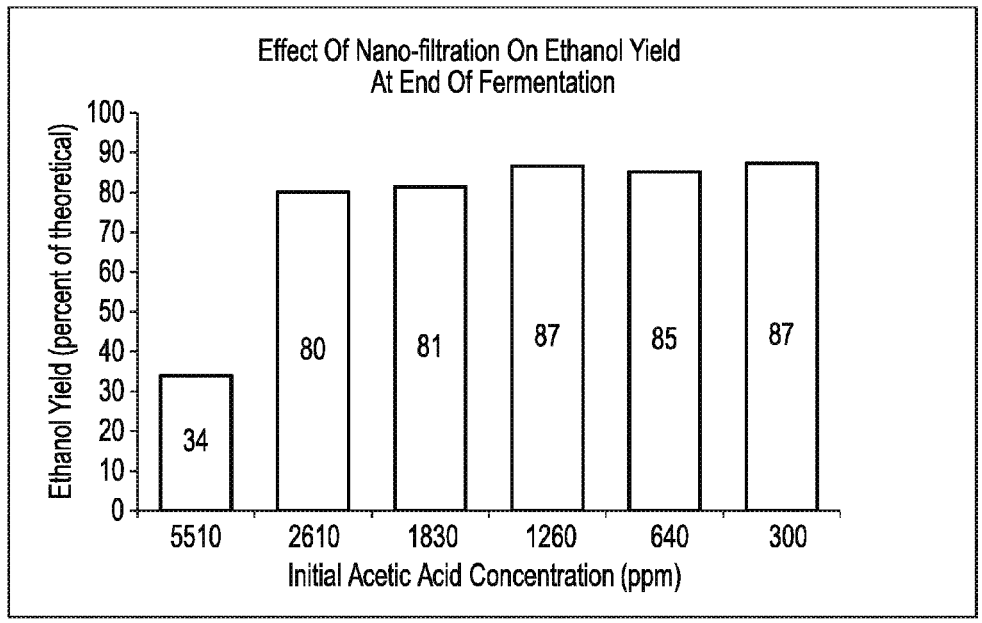

Samples of retentate from Example 2 were collected during diafiltration and were fermented to test the effect of treatment on fermentation efficiency. Samples with different levels of acetic acid were collected, as shown in FIG. 22. The samples were fermented using 10 g/L (dry weight) of a genetically modified strain of *Saccharomyces cerevisiae* yeast (as described in U.S. Pat. No. 7,622,284, assigned to Royal Nedalco B.V.). Each fermentor was supplied with 5 mg/L of Lactoside (available from Lallemand Ethanol Technology, Milwaukee, Wis.), 62.5 g/L urea and 1 g/L yeast extract, and the pH was adjusted to 5.5 using KOH. The fermentations were conducted at 32° C. The fermentors were sampled and tested for xylose and ethanol concentration. The results for 24 hours of fermentation are shown in FIG. 22 and FIG. 15A and FIG. 15B. FIG. 15A illustrate a graph of the effect of nano-filtration on fermentation of liquid component (C5), where fermentation time (in hours) is represented along the horizontal axis and ethanol concentration is represented along the vertical axis. FIG. 15B illustrates the effect of nano-filtration on ethanol yield at the end of fermentation, wherein initial acetic acid concentration is illustrated along the horizontal axis and ethanol yield is represented along the vertical axis.

The sample with an initial acetic acid level of 5510 ppm took longer to finish, and reached an ethanol concentration of 0.8 percent and a yield of 34 percent by 24 hours. It was observed that the samples with lower acetic acid levels performed better. It was also observed that when the initial acetic acid level was 5510 ppm, only 30 percent of the sugar was converted to ethanol by 24 hours, but when the initial acetic acid level was between 1830 and 2610 ppm, a yield of at least 80 percent could be achieved. It was further observed that when the initial acetic acid level was 1260 or less, a yield of at least 85 percent could be achieved.

Example 4

Figure 16A:
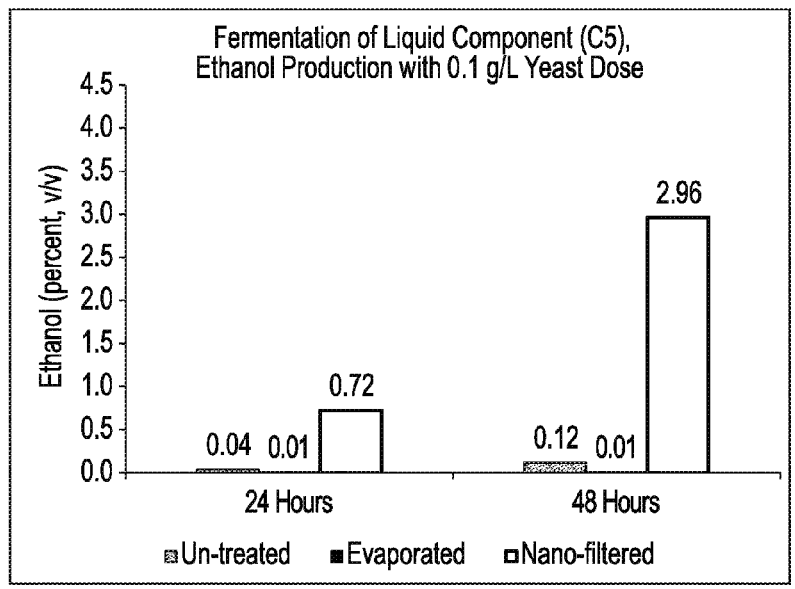
FIG. 16A, FIG. 16B, and FIG. 16C are graphs of the results of treatment of the liquid component according to an exemplary embodiment.
Figure 16B:
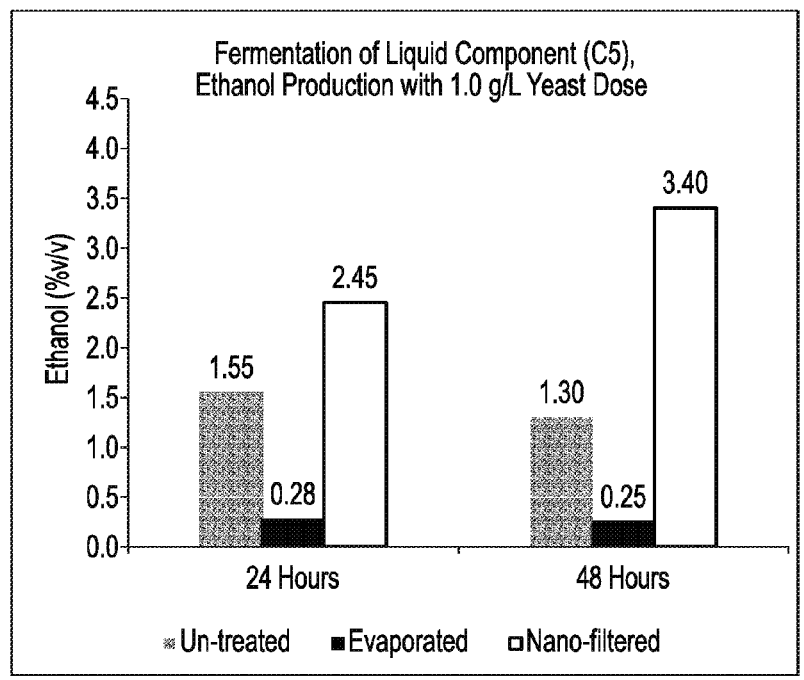
Figure 16C:
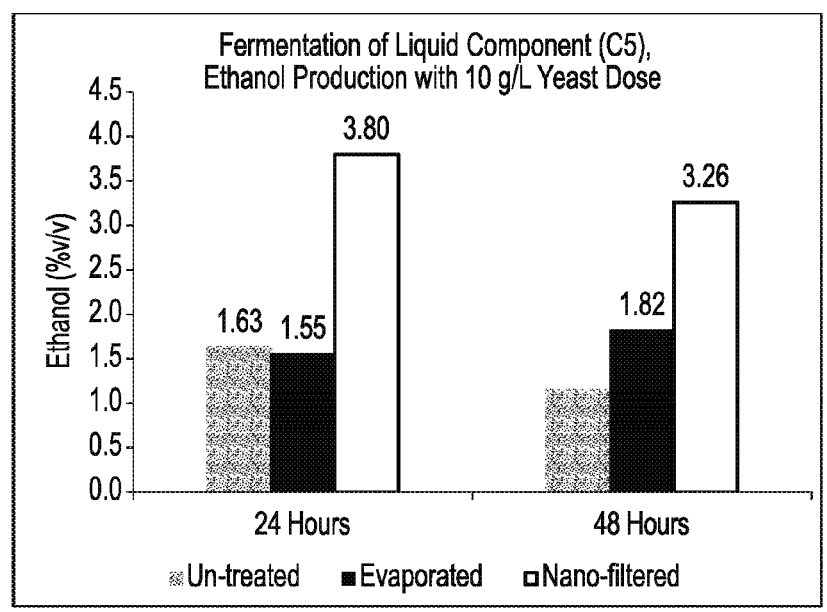

Samples of liquid component were fermented to determine the effect of treatment on fermentation efficiency. Fermentations were set up with varying levels of yeast dosage to determine better operating conditions for fermentation of treated samples. One set of samples were treated using a nano-filtration system as shown in FIG. 12A. Another set of samples were concentrated by approximately 2 fold by evaporation and without nano-filtration. Each fermentor was supplied with either untreated liquid component, nano-filtered liquid component, or concentrated liquid component, and 0.1, 1, or 10 g/L (dry weight) of yeast. The fermentors were also supplied with 5 mg/L of Lactoside (available from Lallemand Ethanol Technology, Milwaukee, Wis.), and the pH was adjusted to 5.5 using KOH. The fermentations were conducted at 32° C. The results are shown in FIG. 23A, FIG. 23B, and FIG. 23C and FIG. 16A, FIG. 16B, and FIG. 16C. FIG. 16A illustrates a graph of the fermentation of liquid component (C5), ethanol production with 0.1 g/L Yeast Dose. FIG. 16B illustrates a graph of the fermentation of liquid component (C5), ethanol production with 1.0 g/L Yeast Dose. FIG. 16C illustrates a graph of the fermentation of liquid component (C5), ethanol production with 10 g/L Yeast Dose. It was observed that the lowest yeast dose of 0.1 g/L was only able to ferment the nano-filtered sample (FIG. 16A). It was also observed (FIG. 16B and FIG. 16C) that the higher yeast doses of 1 g/L and 10 g/L were able to overcome some of the inhibitory effects of the un-treated and the concentrated samples, but the yields were considerably lower than that of the nano-filtered sample.

The embodiments as disclosed and described in the application (including the figures and Examples) are intended to be illustrative and explanatory of the invention. Modifications and variations of the disclosed embodiments, for example, of the apparatus and processes employed (or to be employed) as well as of the compositions and treatments used (or to be used), are possible; all such modifications and variations are intended to be within the scope of the invention.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

What is claimed is:

1. A method for producing a fermentation product from biomass that has been pre-treated in an acid pre-treatment system and separated into a liquid component comprising a first concentration of a pentose and a first amount of at least one acid comprising sulfuric acid, and a first solids component, the method comprising:
    (a) treating the liquid component in a filtration system, the treating comprises: contacting a first nano-filter with the liquid component to form a first retentate and a first permeate, wherein the first retentate comprises a second concentration of the pentose that is greater than the first concentration of the pentose and a second amount of the sulfuric acid that is less than the first amount of the sulfuric acid; and supplying water and the first retentate to a second nano-filter to contact the second nano-filter to form a second retentate and a second permeate, wherein the water supplied to the second nano-filter is in addition to the first retentate, wherein the second retentate comprises a third amount of the sulfuric acid that is less than the second amount the sulfuric acid; and
    (b) combining the second retentate, a fermenting organism, and agents in a fermentation system that ferments the pentose, the fermenting organism, and the agents into a fermentation product;
    (c) recovering the fermentation product from the fermentation system;
    (d) removing water from the first permeate and the second permeate to form a concentrated permeate comprising the sulfuric acid, wherein the removing comprises using a reverse osmosis process; and
    (e) supplying the concentrated permeate for re-use in the acid pre-treatment system; wherein the biomass comprises lignocellulosic material; and wherein the pentose comprises xylose.

2. The method of claim 1, wherein the treating comprises treating the liquid component in a filtration system that comprises a one stage filtration system.

3. The method of claim 1, wherein the treating comprises treating the liquid component in a filtration system that comprises a multiple stage filtration system.

4. The method of claim 3, wherein the treating comprises:
    supplying the liquid component to a first filtration stage to remove a second solids component from the liquid component;
    supplying the liquid component to a second filtration stage to remove acids and to concentrate the xylose in the liquid component; and
    recovering the treated liquid component from the filtration system.

5. The method of claim 4, wherein the supplying the liquid component to the first filtration stage comprises supplying the liquid component to a first filtration stage that comprises a filter with a pore size of 0.01 to 20 micrometers.

6. The method of claim 4, wherein the supplying the liquid component to the second filtration stage comprises supplying the liquid component to a second filtration stage that comprises a nano-filter with a pore size of less than 10 nm.

7. The method of claim 4, wherein the supplying the liquid component to the second filtration stage comprises supplying the liquid component to a second filtration stage, wherein the second filtration stage comprises:
    a first nano-filtration stage; and
    a second nano-filtration stage.

8. The method of claim 7, wherein the supplying the liquid component to the second filtration stage comprises supplying the liquid component to a second filtration stage that comprises a membrane with pores that allow water molecules and acid ions to pass as permeate and retain sugar molecules as retentate.

9. The method of claim 7, wherein the second nano-filtration stage is configured for diafiltration.

10. The method of claim 9, wherein the treating comprises adding water to the liquid component in a ratio of about 0:1 to about 1.3:1 before supplying the retentate.

11. The method of claim 7, wherein the first nano-filtration stage has a permeate flux rate of 1.5 to 35 $L/m^2/h$.

12. The method of claim 1, wherein the treating comprises reducing the concentration of components inhibitory to fermentation in the liquid component, wherein the reducing comprises adjusting at least one pre-treatment condition.

13. The method of claim 1, wherein the fermenting organism comprises yeast capable of converting xylose to ethanol.

14. The method of claim 13, wherein the fermenting organism comprises *Saccharomyces cerevisiae*.

15. The method of claim 13, wherein at least about 75 percent of the xylose is converted to ethanol.

16. The method of claim 1, wherein the treating comprises removing acetic acid from the liquid component.

17. The method of claim 16, wherein the treating comprises removing at least about 60 percent of the acetic acid from the liquid component.

18. The method of claim 1, wherein the treating comprises removing at least about 40 percent of the sulfuric acid from the liquid component.

19. The method of claim 1, wherein the treating comprises concentrating the xylose in the liquid component by at least about 1.5 fold.

20. The method of claim 1, wherein the treating comprises operating the filtration system at a temperature range of about 20° to about 45° C.

21. The method of claim 1, wherein the biomass comprises at least one of corn cobs, corn plant husks, corn plant leaves, and corn plant stalks.

22. The method of claim 1, wherein the biomass consists essentially of corn cobs, corn plant husks, corn plant leaves, and corn plant stalks.

23. The method of claim 1, wherein the liquid component has a pH of about 3 or less.

24. The method of claim 1, wherein the liquid component has a pH of about 1 to about 2.

25. A method of reducing the concentration of sulfuric acid in a pentose composition derived from a pre-treated biomass comprising:
   providing a pre-treated lignocellulosic biomass material, wherein the pre-treated lignocellulosic biomass has been subjected to a sulfuric acid hydrolysis process to hydrolyse hemicellose to provide pentose, and wherein the pre-treated biomass comprises a first liquid component comprising the sulfuric acid and the pentose, and a solids component;
   separating the liquid component from the solids component, wherein the liquid component has a first weight ratio of the pentose to the sulfuric acid;
   contacting a nano-filter with the liquid component to form a first retentate and a first permeate, wherein the first retentate comprises a second weight ratio of the pentose to the sulfuric acid and wherein the second weight ratio is greater than the first weight ratio;
   mixing the first retentate with water to form a second liquid component;
   contacting a nano-filter with the second liquid component to form a second retentate and a second permeate, wherein the second retentate comprises a third weight ratio of the pentose to the sulfuric acid and wherein the third weight ratio is greater than the second weight ratio, and fermenting the second retentate into a fermentation product.

\* \* \* \* \*